(12) United States Patent
Takehara et al.

(10) Patent No.: US 11,024,410 B2
(45) Date of Patent: Jun. 1, 2021

(54) MUSCLE CONDITION CHANGE DETERMINATION APPARATUS, MUSCLE CONDITION CHANGE DETERMINATION METHOD, AND RECORDING MEDIUM

(71) Applicant: TANITA CORPORATION, Tokyo (JP)

(72) Inventors: Tomoko Takehara, Tokyo (JP); Satsuki Yukino, Tokyo (JP); Tomoka Shimizu, Tokyo (JP); Masataka Takesada, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 982 days.

(21) Appl. No.: 14/872,738

(22) Filed: Oct. 1, 2015

(65) Prior Publication Data

US 2016/0106356 A1 Apr. 21, 2016

(30) Foreign Application Priority Data

Oct. 21, 2014 (JP) .............................. JP2014-214494

(51) Int. Cl.
*G16H 20/30* (2018.01)
*A61B 5/22* (2006.01)
*A61B 5/00* (2006.01)
*A61B 5/053* (2021.01)
*G16H 50/20* (2018.01)
(Continued)

(52) U.S. Cl.
CPC ........... *G16H 20/30* (2018.01); *A61B 5/0004* (2013.01); *A61B 5/053* (2013.01); *A61B 5/0537* (2013.01); *A61B 5/22* (2013.01); *A61B 5/224* (2013.01); *A61B 5/4519* (2013.01); *A61B 5/486* (2013.01); *A61B 5/4866* (2013.01); *A61B 5/72* (2013.01); *A61B 5/7275* (2013.01); *A61B 5/742* (2013.01); *G16H 50/20* (2018.01); *G16H 20/60* (2018.01)

(58) Field of Classification Search
CPC ....................................................... A61B 5/224
See application file for complete search history.

(56) References Cited

U.S. PATENT DOCUMENTS

2004/0225237 A1  11/2004 Keren
2005/0177060 A1   8/2005 Yamazaki et al.
(Continued)

FOREIGN PATENT DOCUMENTS

JP   2010-46230 A    3/2010
JP   2013-180122 A   9/2013
(Continued)

OTHER PUBLICATIONS

Communication dated Mar. 17, 2016 from European Patent Office in counterpart Application No. 15188976.3.
(Continued)

*Primary Examiner* — Daniel L Cerioni
*Assistant Examiner* — Yasmeen S Warsi
(74) *Attorney, Agent, or Firm* — Sughrue Mion, PLLC

(57) ABSTRACT

A muscle condition change determination apparatus includes a circuit. The circuit configures: a change information acquisition unit; and a type determination unit. The change information acquisition unit acquires change information indicating changes in a plurality of muscle indicators. The type determination unit determines the type of change in a muscle condition according to the change information.

18 Claims, 18 Drawing Sheets

(51) Int. Cl.
*A61B 5/0537* (2021.01)
*G16H 20/60* (2018.01)

(56) References Cited

U.S. PATENT DOCUMENTS

| | | | |
|---|---|---|---|
| 2006/0199155 A1* | 9/2006 | Mosher | G09B 19/0092 434/127 |
| 2010/0331629 A1* | 12/2010 | Sato | A61B 5/0537 600/300 |
| 2011/0319735 A1 | 12/2011 | Hill | |
| 2012/0071732 A1 | 3/2012 | Grey et al. | |
| 2012/0329749 A1 | 12/2012 | Smith et al. | |
| 2014/0272853 A1 | 9/2014 | Sakai et al. | |

FOREIGN PATENT DOCUMENTS

| | | |
|---|---|---|
| WO | 95/13290 A1 | 5/1995 |
| WO | 2013/160549 A1 | 10/2013 |

OTHER PUBLICATIONS

Communication dated Jun. 12, 2018 from the Japanese Patent Office in counterpart application No. 2014-214494.

* cited by examiner

FIG. 14

| MUSCLE CONDITION | DETERMINATION BASIS | CAUSE AND PHENOMENON | CATEGORY OF NUTRITION |
|---|---|---|---|
| MUSCLE STRENGTH DECREASE | $\Delta\% \ F/w < 0$ (STRENGTH WHICH MUSCLE CAN OUTPUT) | INFORMATION TRANSMISSION QUANTITY DECREASE NERVE DEGRADATION MUSCLE FIBER COMPOSITION RATIO DEGRADATION MANY CELLS | (1) NUTRITION FOR BRAIN |
| MUSCLE POWER DECREASE | $\Delta\% \ RFD/w < 0$ (MUSCLE STRENGTH / TIME) | INSTANTANEOUS FORCE REDUCTION | (2) MUSCLE CONTRACTION |
| MUSCLE QUALITY DECREASE (MUSCLE ATROPHY) | $\Delta\% \ R/X < 0$ (MUSCLE FIBER COMPOSITION RATIO) | MUSCLE FIBER COMPOSITION RATIO DEGRADATION MANY CELLS | (3) MUSCLE CELL |
| MUSCLE QUANTITY DECREASE | $\Delta\% \ \text{MUSCLE QUANTITY}/Ht^2 < 0$ (MUSCLE QUANTITY) | MUSCLE CELL REDUCTION | (4) MUSCLE GLYCOGEN |

FIG. 15

|   | (1) | (2) | (3) | (4) |
|---|-----|-----|-----|-----|
| A | ▓ | ▓ | ▓ | ▓ |
| B | ▓ | ▓ | ▓ |   |
| C | ▓ | ▓ |   |   |
| D | ▓ |   | ▓ | ▓ |
| E | ▓ |   | ▓ |   |
| F | ▓ |   |   |   |
| G |   | ▓ | ▓ | ▓ |
| H |   | ▓ | ▓ |   |
| I |   | ▓ |   |   |
| J |   |   | ▓ | ▓ |
| K |   |   | ▓ |   |
| L |   |   |   | ▓ |
| M |   |   |   |   |

FIG. 16

| CATEGORY OF NUTRITION | MAIN NUTRITION | METABOLIC NUTRITION |
|---|---|---|
| (1) NUTRITION FOR BRAIN | · TRYPTOPHAN (SEROTONINE)<br>· PHENYLALANINE, TYROSINE (DOPAMINE)<br>· GABA (γ-AMINOBUTYRIC ACID)<br>· (LEUCINE) | +VITAMIN B6, VITAMIN B2, MAGNESIUM<br>+VITAMIN B6, NICOTINE ACID (B3), VITAMIN C, COPPER, IRON<br>+VITAMIN B6, MAGNESIUM<br>+VITAMIN B6 |
| (2) MUSCLE CONTRACTION | · MAGNESIUM<br>· POTASSIUM<br>· SODIUM | — |
| (3) MUSCLE CELL | · LEUCINE | +VITAMIN B6 |
| (4) MUSCLE GLYCOGEN | · CALORIE<br>· INTAKE OF CARBOHYDRATE AFTER WORKOUT IN THE MORNING<br>· BRANCHED CHAIN AMINO ACID | +VITAMIN B1 (+ALLICIN)<br>+VITAMIN B6 |

FIG. 17

| NUTRITION | INGREDIENT |
|---|---|
| TRYPTOPHAN | BANANA<br>SOYMILK<br>MILK<br>YOGURT |
| PHENYLALANINE | SOYBEAN (SOYBEAN PRODUCT)<br>WHEAT (HARD FLOUR)<br>KOYADOFU (FREEZE-DRIED TOFU)<br>EGG |
| GABA | TOMATO<br>POTATO |
| LEUCINE | LIVER<br>HORSE MACKEREL OR SALMON<br>DAIRY PRODUCT |
| BRANCHED CHAIN AMINO ACID | CHICKEN BREAST<br>TUNA<br>BONITO |
| VITAMIN B1 | WHEAT GERM, BROWN RICE<br>PORK<br>BUCKWHEAT |
| VITAMIN B2 | LIVER<br>EEL<br>MILK |
| VITAMIN B6 | LEAN FISH (TUNA, BONITO, AND THE LIKE)<br>MEAT (PORK, CHICKEN, BEEF, AND THE LIKE)<br>LIVER (SWINE, CHICKEN, COW)<br>BEAN (SOYBEAN, ADZUKI BEAN, AND THE LIKE)<br>FRUIT (BANANA, PRUNE, AND THE LIKE) |
| ALLICIN | GARLIC<br>LEEK<br>ONION |
| ⋮ | ⋮ |

MUSCLE CONDITION CHANGE DETERMINATION APPARATUS, MUSCLE CONDITION CHANGE DETERMINATION METHOD, AND RECORDING MEDIUM

CROSS-REFERENCE TO RELATED APPLICATIONS

Priority is claimed on Japanese Patent Application No. 2014-214494, filed on Oct. 21, 2014, the contents of which are incorporated herein by reference.

BACKGROUND

Field of the Invention

The present invention relates to a muscle condition change determination apparatus, a muscle condition change determination method, and a recording medium.

Background

Techniques that evaluate a muscle condition such as muscle strength have been proposed.

For example, a lower limb determination apparatus disclosed in Japanese Patent Application, Publication No. JP2013-180122A includes an information acquisition unit that acquires input information including a measurement body weight ratio indicating lower limb muscle strength per the body weight of a subject, a storage unit that includes a first evaluation value indicating a body weight ratio and the degree of risk that makes walking difficult and stores a body-weight-ratio first-evaluation-value relationship indicating a relationship between a body weight ratio and a first evaluation value, and a determination unit that outputs a correspondence evaluation value corresponding to the input information based on the body-weight-ratio first-evaluation-value relationship.

Japanese Patent Application, Publication No. JP2013-180122A discloses that thereby, it is easier for a subject to recognize a measurement value relating to lower limb physical strength such as a body weight ratio.

SUMMARY

Muscles are classified into some types such as fast muscles (fast twitch muscles) and slow muscles (slow twitch muscles). It is believed that the treatments effective at treating problems with fast muscles and slow muscles are different. If muscle problems can be classified correctly, there is a possibility that an effective treatment therefor can be determined.

An aspect of the present invention provides a muscle condition change determination apparatus, a muscle condition change determination method, and a program capable of classifying muscle problems.

According to a first aspect of the present invention, a muscle condition change determination apparatus includes a circuit, the circuit configuring: a change information acquisition unit; and a type determination unit, wherein the change information acquisition unit acquires change information indicating changes in a plurality of muscle indicators, and the type determination unit determines the type of change in a muscle condition according to the change information.

The circuit may further configure a treatment determination unit, and the treatment determination unit may determine a treatment for the change in the muscle condition according to the type of change in the muscle condition determined by the type determination unit.

The treatment determination unit may determine a recommended exercise.

The treatment determination unit may determine a recommended meal.

The change information acquisition unit may acquire, as the change information, information indicating a change in muscle strength, a change in muscle power, a change in muscle quality, and a change in muscle quantity.

The type determination unit may determine the type of change in the muscle condition by using a determination basis selected in response to the age of a determination subject.

According to a second aspect of the present invention, a muscle condition change determination method includes: acquiring change information indicating changes in a plurality of muscle indicators; and determining the type of change in a muscle condition according to the change information.

A third aspect of the present invention is a non-transitory computer-readable recording medium including a program that causes a computer to: acquire change information indicating changes in a plurality of muscle indicators; and determine the type of change in a muscle condition according to the change information.

According to an aspect of the present invention, it is possible to classify muscle problems.

BRIEF DESCRIPTION OF THE DRAWINGS

FIG. 14 is a view showing a relationship between a muscle condition and a category of required nutrition.

FIG. 15 is a view showing a relationship between the type of change in a muscle condition and the category of nutrition in the embodiment.

FIG. 16 is a view of showing a relationship between the category of nutrition and a specific nutrition.

FIG. 17 is a view showing a relationship between nutrition and ingredients.

DESCRIPTION OF THE EMBODIMENTS

Hereinafter, an embodiment of the present invention is described; however, the claimed invention is not limited to the following embodiment. Further, all of the combinations of features described in the embodiment are not necessary for means for solving the problems of the invention.

Figure 1:
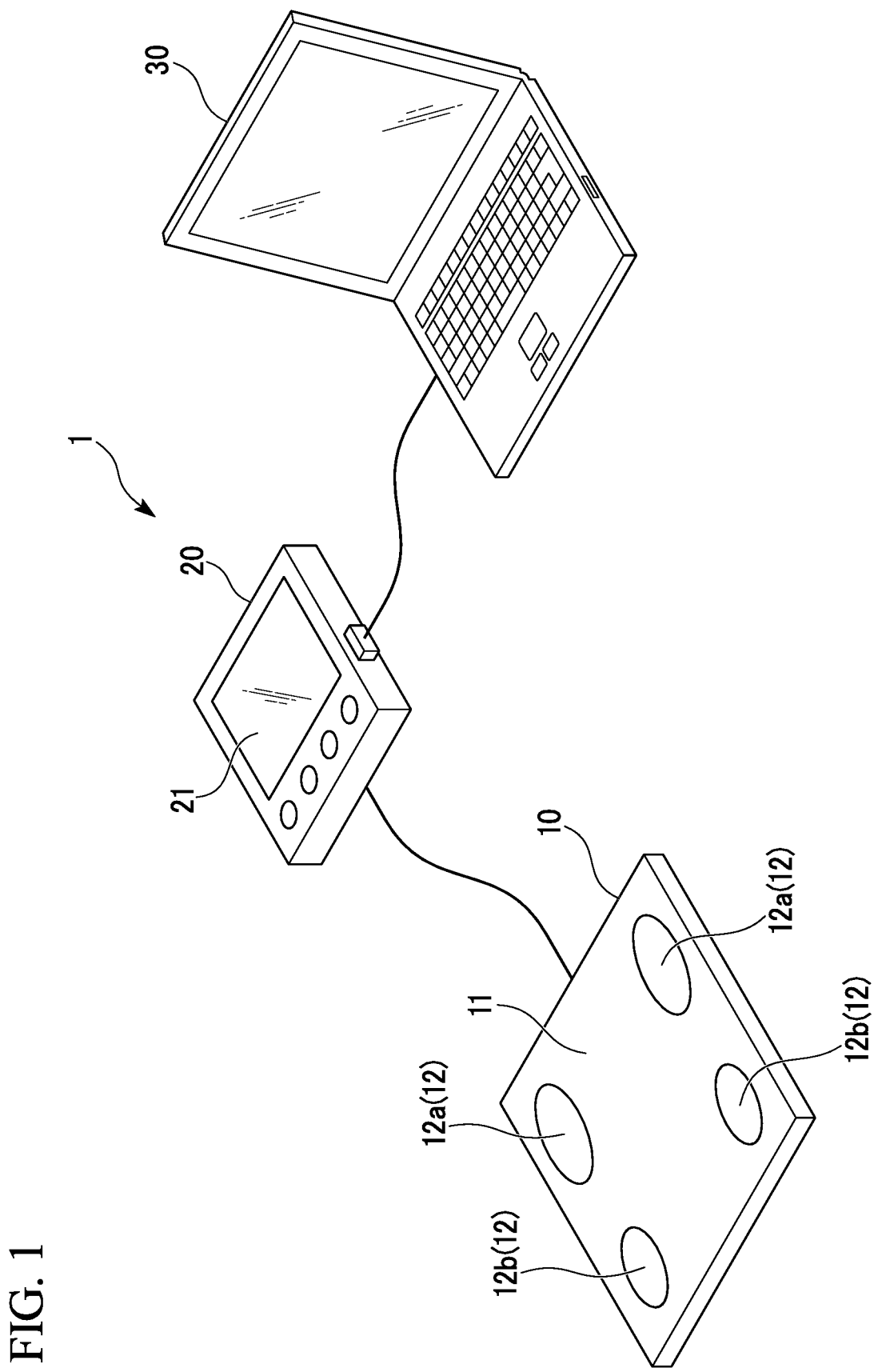
FIG. 1 is a schematic configuration view showing an apparatus configuration of a motor function determination system in an embodiment of the present invention.

FIG. 1 is a schematic configuration view showing an apparatus configuration of a motor function determination system including a process apparatus as an example of a muscle condition change determination apparatus in an embodiment of the present invention. In FIG. 1, a motor function determination system 1 includes a measurement apparatus 10 and a process apparatus 20. Further, FIG. 1 shows a measurement base 11 included in the measurement apparatus 10, a current supplying electrode 12a, a voltage measuring electrode 12b, and a display screen of a display device 21 included in the process apparatus 20. Further, a personal computer (PC) 30 is connected to the process apparatus 20. The current supplying electrode 12a and the voltage measuring electrode 12b are collectively referred to as an electrode 12.

The motor function determination system 1 determines the type of change in a muscle condition of a user of the motor function determination system 1 corresponds to any of thirteen types shown in FIG. 9 and FIG. 10 described later. Then, the motor function determination system 1 determines a treatment for the change in a muscle condition based on the determination result and presents the treatment to the user. Here, a muscle condition represents a condition of muscle.

The measurement apparatus 10 is an apparatus for measuring the bioelectrical impedance and the body weight of the user.

The measurement base 11 is provided on the upper surface of the measurement apparatus 10, and the electrode 12 is provided on the measurement base 11. The measurement apparatus 10 measures a load applied to the measurement base 11. Further, the measurement apparatus 10 measures the bioelectrical impedance of the user by using the electrode 12.

Figure 9:
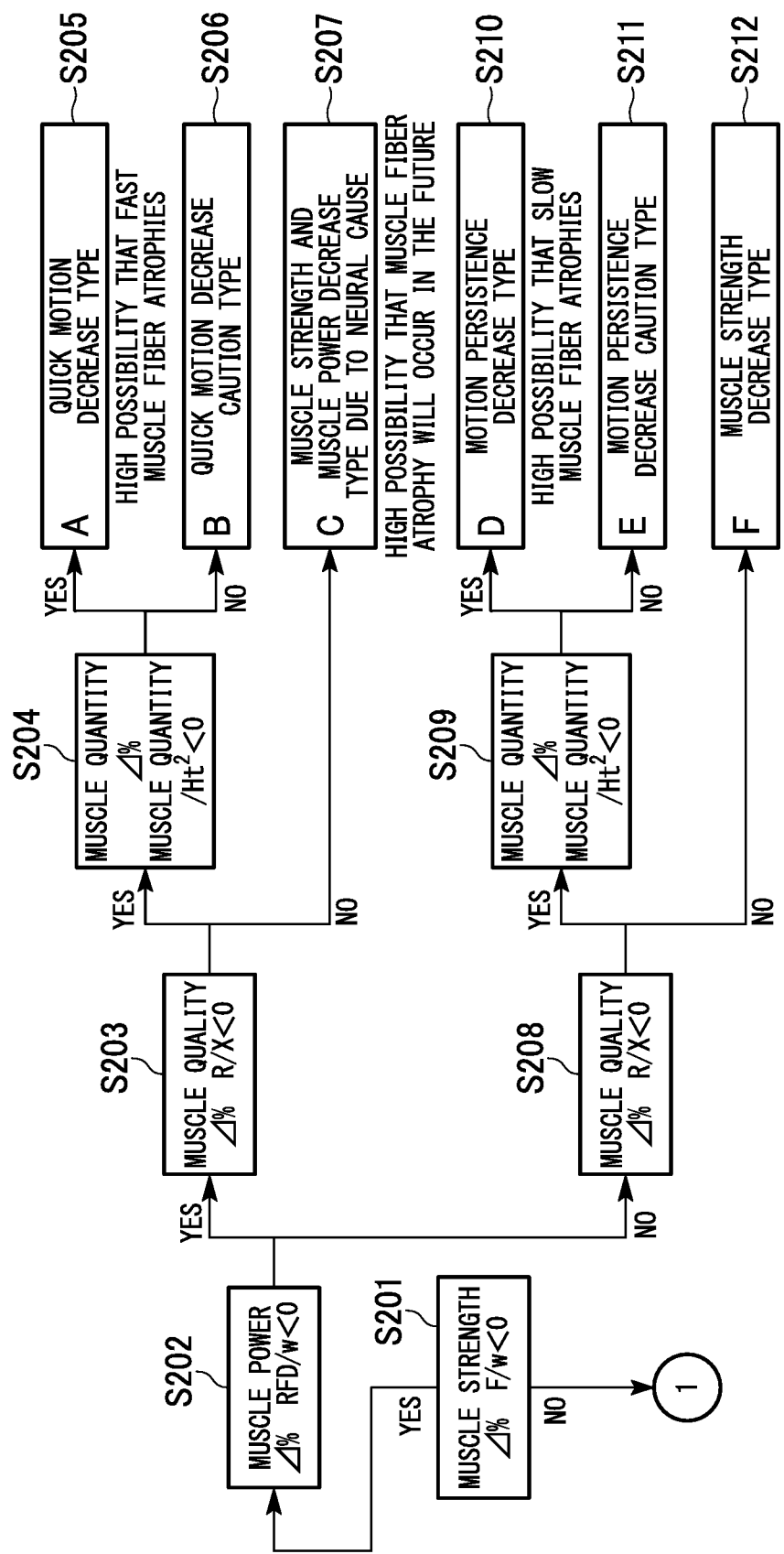
FIG. 9 is a view showing an example of a process sequence of a type determination of the change in a muscle condition of a user performed by a type determination unit in the embodiment.
Figure 10:
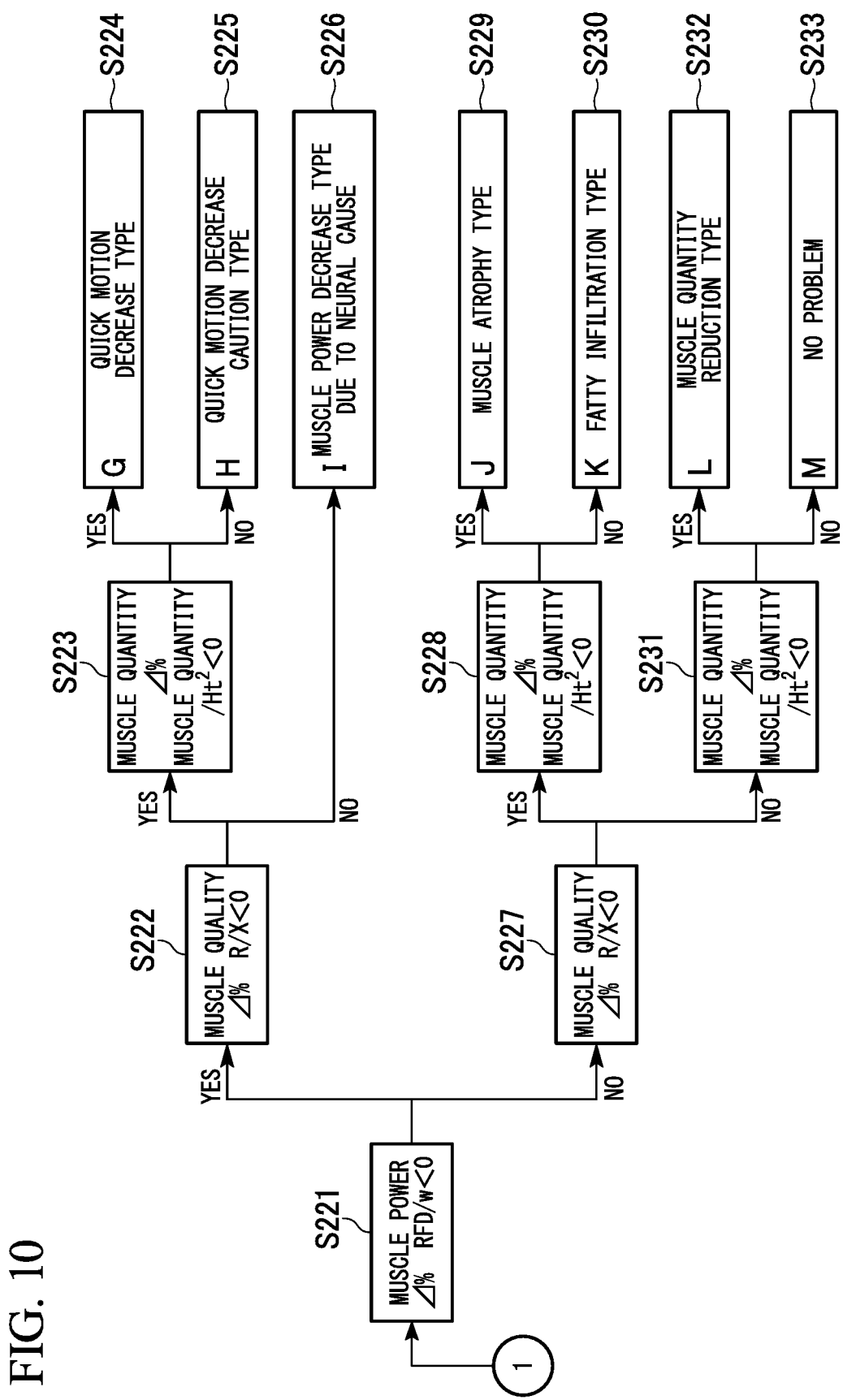
FIG. 10 is a view showing an example of a process sequence of a type determination of the change in a muscle condition of a user performed by the type determination unit in the embodiment.

The process apparatus 20 determines to which one of thirteen types shown in FIG. 9 and FIG. 10 the type of change in the muscle condition of the user corresponds based on the measurement value of the measurement apparatus 10. Then, the process apparatus 20 determines a treatment for the change in the muscle condition (specifically, a treatment for reducing the weakening of muscle) such as an exercise and a recipe recommended for the user depending on the determination result and displays the treatment on the display screen of the display device 21.

The process apparatus 20 may be configured as a dedicated apparatus. Alternatively, a generic information processing apparatus such as a personal computer may execute a program to thereby configure the process apparatus 20.

Further, as shown in FIG. 1, the process apparatus 20 may be, for example, connectable to another apparatus such as a personal computer. Specifically, the process apparatus 20 may be capable of transmitting information to another apparatus such as transmitting one of or both of the determination result of the type of change in the muscle condition and the determined treatment to another apparatus.

The measurement apparatus 10 and the process apparatus 20 may be integrated as one apparatus. Alternatively, one of or both of the measurement apparatus 10 and the process apparatus 20 may be further subdivided to be configured as a plurality of apparatuses.

Figure 2:
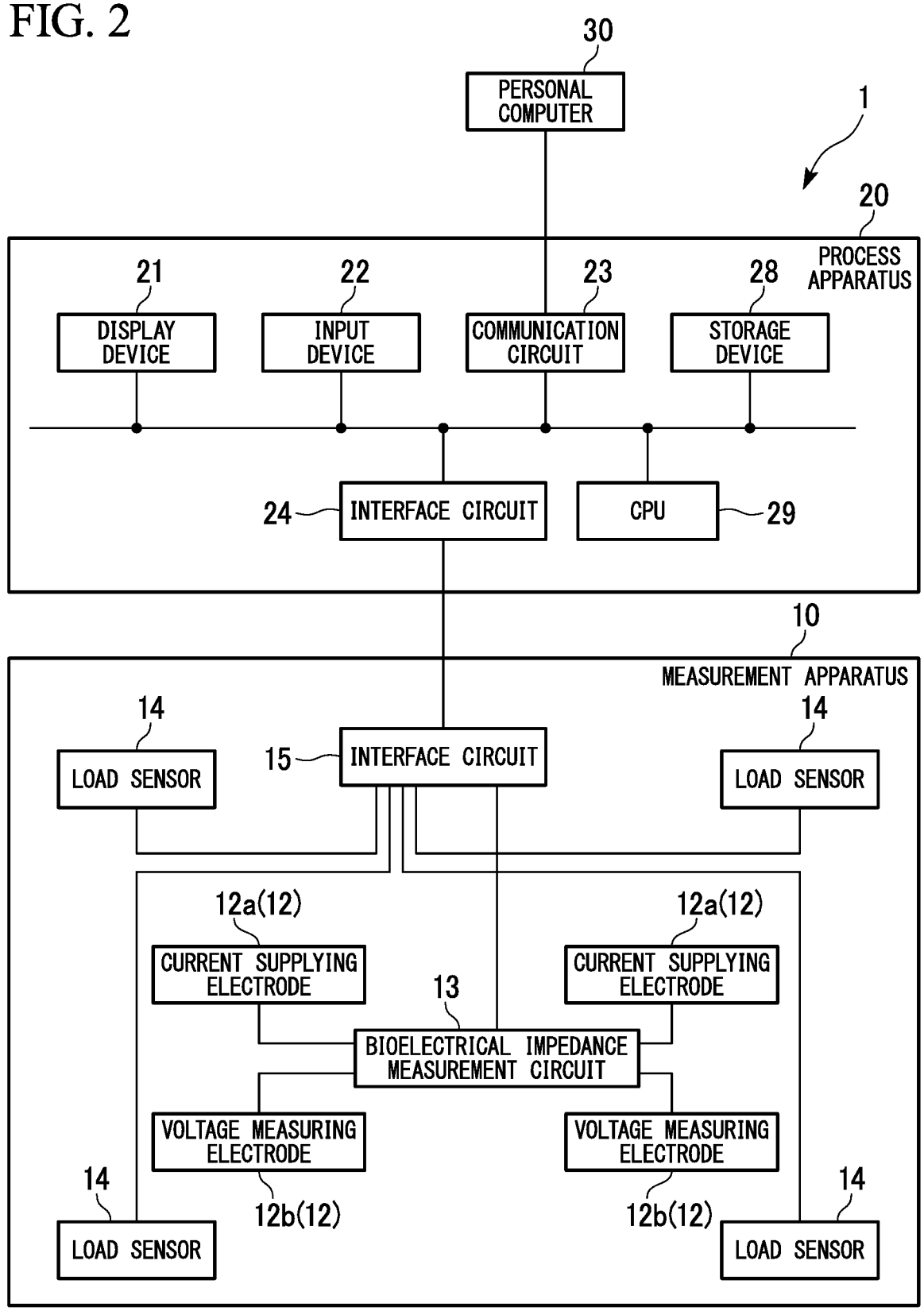
FIG. 2 is a schematic block diagram showing a hardware configuration of the motor function determination system in the embodiment.

FIG. 2 is a schematic block diagram showing a hardware configuration of the motor function determination system 1. In FIG. 2, the motor function determination system 1 includes the measurement apparatus 10 and the process apparatus 20. The measurement apparatus 10 includes the current supplying electrode 12a, the voltage measuring electrode 12b, a bioelectrical impedance measurement circuit 13, a load sensor 14, and an interface circuit 15. The process apparatus 20 includes the display device 21, an input device 22, a communication circuit 23, an interface circuit 24, a storage device 28, and a CPU 29 (circuit, circuitry).

Further, similar to the case of FIG. 1, the personal computer 30 is connected to the process apparatus 20.

In the measurement apparatus 10, right and left current supplying electrodes 12a apply a weak electric current to a user's body.

Right and left voltage measuring electrodes 12b detect a potential difference (voltage) occurring between the voltage measuring electrodes 12b.

The bioelectrical impedance measurement circuit 13 measures a bioelectrical impedance in a state where a user is standing such that the user's left bare foot comes into contact with both of the left current supplying electrode 12a and the left voltage measuring electrode 12b and the user's right bare foot comes into contact with both of the right current supplying electrode 12a and the right voltage measuring electrode 12b. Specifically, the bioelectrical impedance measurement circuit 13 applies a weak AC current to the right and left current supplying electrodes 12a, detects a voltage (potential difference) through the right and left voltage measuring electrodes 12b, and obtains a bioelectrical impedance (impedance Z, a resistance component R and a reactance component X of the impedance Z) of the user based on the current and the voltage. The resistance component R and the reactance component X of the impedance Z are obtained by performing a waveform processing such as a discrete Fourier transform (DFT) processing using the applied current and the detected voltage at this time.

Then, the process apparatus 20 obtains a user's body composition indicator (for example, a body fat percentage and the like) based on the obtained bioelectrical impedance.

One of the load sensors 14 is arranged at each of positions close to the four corners of the rectangular measurement base 11 (FIG. 1) and measures a load in each of the positions. Each of the load sensors 14 measures the load, and thereby it is possible to measure the load applied to the measurement base 11 and the balance (position of the center of gravity in the measurement base 11).

The number and the arrangement of the load sensors 14 may be those with which it is possible to measure the load applied to the measurement base 11 and the balance. For example, three load sensors 14 may be arranged to surround the electrode 12, and the load applied to the measurement base 11 may be supported by the three load sensors.

The process apparatus 20 calculates the user's body weight and the position of the center of gravity in the measurement base 11 based on the load measured by each of the load sensors 14.

The interface circuit 15 includes a connection terminal of a signal line and exchanges data with the interface circuit 24 of the process apparatus 20 via the signal line. Specifically, the interface circuit 15 transmits the bioelectrical impedance measured by the bioelectrical impedance measurement circuit 13 and the load measured by each of the load sensors 14, to the interface circuit 24.

The method of exchanging data between the measurement apparatus 10 and the process apparatus 20 is not limited to a wired method. The interface circuit 15 may perform a wireless communication with the interface circuit 24.

In the process apparatus 20, the display device 21 includes a display screen and displays a variety of images. Specifically, the process apparatus 20 displays a determination result of the type of change in the muscle condition of the user and a treatment for the change in the muscle condition. As the display device 21, various display devices such as a liquid crystal panel, an organic electro-luminescence (EL) panel, or a LED panel can be used.

The input device 22 accepts a variety of user operations such as an input operation of biological information of the user such as the body height, age, and sex of the user. As the input device 22, a touch sensor that is provided on the display screen of the display device 21 and configures a touch panel may be used. Alternatively, as the input device 22, another input device such as one of or the combination of a keyboard and a mouse may be used in addition to or in place of the touch sensor.

The communication circuit 23 includes a connection terminal of a signal line and exchanges data with another apparatus connected via the signal line. Specifically, the communication circuit 23 transmits one of or both of the determination result of the type of change in the muscle condition and the treatment for the change in the muscle condition, to another apparatus.

The method with which the communication circuit 23 exchanges data with another apparatus is not limited to a wired method.

The communication circuit 23 may perform a wireless communication with another apparatus.

The interface circuit 24 includes a connection terminal of a signal line and exchanges data with the interface circuit 15 of the measurement apparatus 10 via the signal line. Specifically, the interface circuit 24 receives the bioelectrical impedance measured by the bioelectrical impedance measurement circuit 13 and the load measured by each of the load sensors 14, from the interface circuit 15.

The storage device 28 stores a variety of data. Specifically, the storage device 28 stores the history of each of a muscle strength indicator, a muscle power indicator, a muscle quality indicator, and a muscle quantity indicator, calculated by the CPU 29. The history stored in the storage device 28 is used for the CPU 29 to calculate the change rate of muscle strength indicator, the change rate of muscle power indicator, the change rate of muscle quality indicator, and the change rate of muscle quantity indicator.

The muscle strength indicator, the muscle power indicator, the muscle quality indicator, and the muscle quantity indicator correspond to an example of muscle indicators (muscle condition indicators). Here, the muscle indicator is a value indicating a muscle condition. The change rate of muscle strength indicator, the change rate of muscle power indicator, the change rate of muscle quality indicator, and the change rate of muscle quantity indicator correspond to an example of change information indicating changes in a plurality of muscle indicators.

The muscle strength indicator and the muscle power indicator are indicators represented from the functional viewpoint of muscle. The muscle quality indicator and the muscle quantity indicator are indicators represented from the structural viewpoint of muscle.

The muscle indicator which the motor function determination system 1 uses to determine the type of change in the muscle condition is not limited to the muscle strength indicator, the muscle power indicator, the muscle quality indicator, and the muscle quantity indicator and can be another muscle indicator. Further, the number of muscle indicators which the motor function determination system 1 uses to determine the type of change in the muscle condition is not limited to four and may be two or more.

The storage device 28 may be an internal storage device of the measurement apparatus 10, may be an external storage device attached externally to the measurement apparatus 10, and may be configured to include both of an internal storage device and an external storage device.

The CPU 29 reads out a program from the storage device 28, executes the program, and thereby performs a variety of processes.

Figure 3:
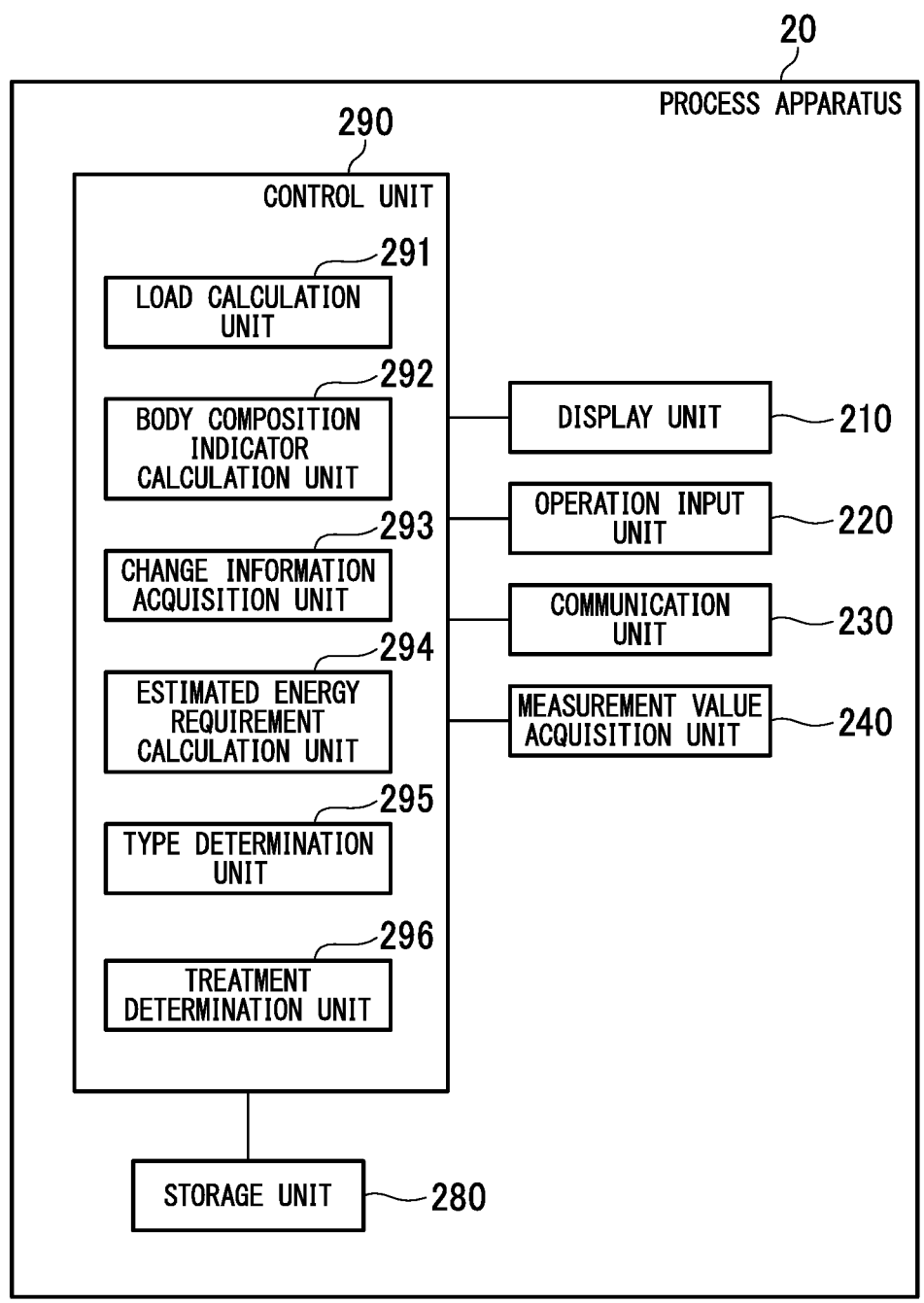
FIG. 3 is a schematic block diagram showing a functional configuration of a process apparatus in the embodiment.

FIG. 3 is a schematic block diagram showing a functional configuration of the process apparatus 20. In FIG. 3, the process apparatus 20 includes a display unit 210, an operation input unit 220, a communication unit 230, a measurement value acquisition unit 240, a storage unit 280, and a control unit 290. The control unit 290 includes a load calculation unit 291, a body composition indicator calculation unit 292, a change information acquisition unit 293, an estimated energy requirement calculation unit 294, a type determination unit 295, and a treatment determination unit 296.

The display unit 210 is configured by using the display device 21 and displays a variety of images.

The operation input unit 220 is configured by using the input device 22 and accepts a user operation.

The communication unit 230 is configured by using the communication circuit 23 and communicates with another apparatus.

The measurement value acquisition unit 240 is configured by using the interface circuit 24 and receives the bioelectrical impedance measured by the bioelectrical impedance measurement circuit 13 and the load measured by each of the load sensors 14 from the measurement apparatus 10.

The storage unit 280 is configured by using the storage device 28 and stores a variety of information.

The control unit 290 controls each unit of the process apparatus 20 and performs a variety of processes. The control unit 290 is configured by the CPU 29 reading out a program from the storage device 28 to execute the program.

The load calculation unit 291 subtracts the weight of the measurement base 11 from the sum of the load measured by the four load sensors 14 and calculates the load on the measurement base 11. That is, the load calculation unit 291 shows the difference between the sum of the four load sensors when a user is on the measurement base and the sum of the four load sensors when the user is not on the measurement base as the body weight of the user.

The body composition indicator calculation unit 292 obtains a user's body composition indicator (for example, a body fat percentage and the like) based on the bioelectrical impedance which the interface circuit 24 receives from the measurement apparatus 10.

The change information acquisition unit 293 acquires the change rate of muscle strength indicator, the change rate of muscle power indicator, the change rate of muscle quality indicator, and the change rate of muscle quantity indicator. As described above, these values correspond to an example of change information.

The change information acquisition unit 293 acquires biological information of a user which the input device 22 accepts an input operation and stores the biological information in the storage unit 280. Then, the change information acquisition unit 293 calculates each of the muscle strength indicator, the muscle power indicator, the muscle quality indicator, and the muscle quantity indicator based on the bioelectrical impedance acquired by the measurement value acquisition unit 240 and the load calculated by the load calculation unit 291, and further, if necessary, based on the biological information of the user and stores the calculated value in the storage unit 280.

Further, the change information acquisition unit 293 reads out a past value (for example, the last value) of muscle strength indicator from the storage unit 280, subtracts the past value from the calculated current value, divides the reduction result by the past value, multiplies the division result by 100, and thereby calculates the change rate of muscle strength indicator. Similarly, the change information acquisition unit 293 calculates the change rate of each of the muscle power indicator, the muscle quality indicator, and the muscle quantity indicator.

As the past value (past value of muscle strength indicator, past value of muscle power indicator, past value of muscle quality indicator, and past value of muscle quantity indicator) used by the change information acquisition unit 293, for example, past values of various times such as three months ago, six months ago, or one year ago can be used.

The estimated energy requirement calculation unit 294 calculates an estimated energy requirement. Here, the estimated energy requirement is a habitual energy intake per day which is estimated to provide the highest probability that the incoming and outgoing of energy becomes zero.

The type determination unit 295 determines the type of change in the muscle condition corresponds to any of the thirteen types shown in FIG. 9 and FIG. 10 described later according to the change information acquired by the change information acquisition unit 293.

The type determined by the type determination unit 295 is not limited to those shown in FIG. 9 and FIG. 10. For example, as described later with reference to FIG. 11, the type determination unit 295 may determine the type of change in the muscle condition for elderly people. Alternatively, as described later with reference to FIG. 12 and FIG. 13, the type determination unit 295 may determine the type of change in the muscle condition based on the evaluation depending on the age of the user.

The treatment determination unit 296 determines a treatment against the change in the muscle condition according to the type of change in the muscle condition determined by the type determination unit 295. Specifically, the treatment determination unit 296 determines one of or both of a recommended exercise and a recommended meal.

Next, a process performed by the motor function determination system 1 is described.

Figure 4:
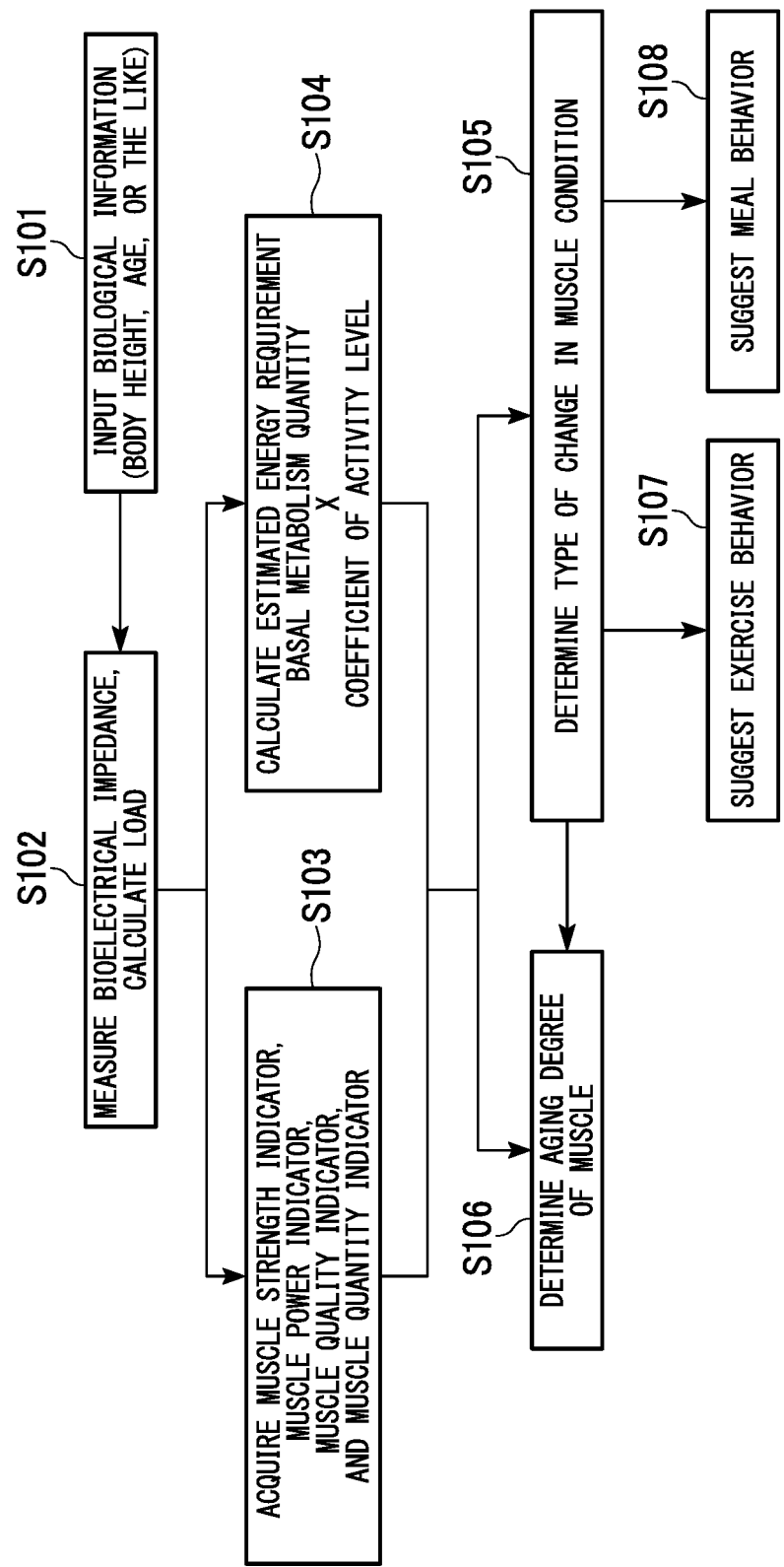
FIG. 4 is a view showing an example of a process sequence performed by the motor function determination system in the embodiment.

FIG. 4 is a view showing an example of a process sequence performed by the motor function determination system 1.

In the process of FIG. 4, the operation input unit 220 accepts an input of biological information relating to a user such as the body height, age, and sex of the user, and a reply to a questionnaire relating to the amount of activity of the user (step S101). Then, the change information acquisition unit 293 acquires the biological information and stores the biological information in the storage unit 280. When the storage unit 280 already stores the biological information, the change information acquisition unit 293 may read out the biological information from the storage unit 280 in place of an input of the biological information to the operation input unit 220 in step S101. Thereby, it is not necessary for the user to perform an input operation of biological information, and in this regard, it is possible to reduce the burden of the user.

Next, the bioelectrical impedance measurement circuit 13 measures the bioelectrical impedance of the user, and the load calculation unit 291 calculates the load such as the body weight of the user (step S102).

Figure 5:
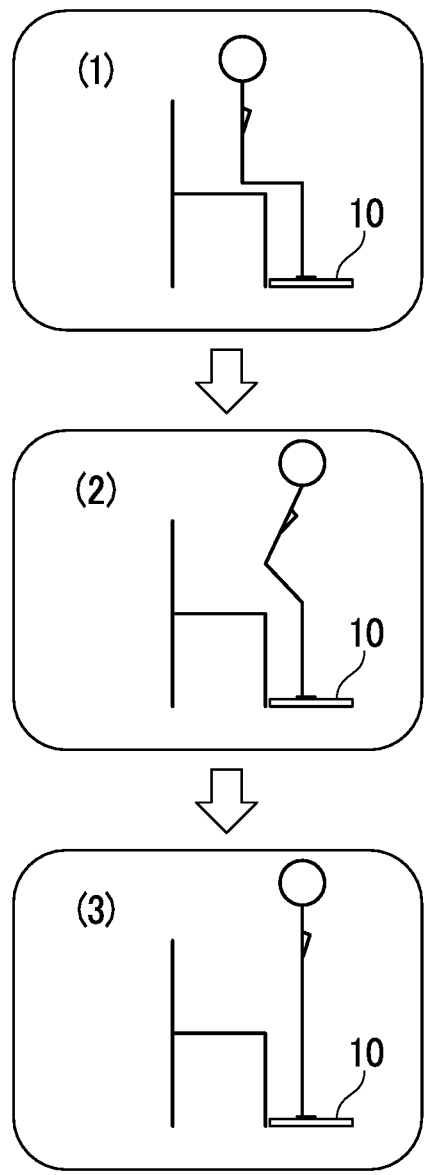
FIG. 5 is a view showing the motion of a user when a bioelectrical impedance is measured and a load is calculated in the embodiment.

FIG. 5 is a view showing the motion of the user when the bioelectrical impedance is measured and the load is calculated.

The user sits on a chair provided at a position close to the measurement apparatus 10 in a state where the user puts the user's feet on the measurement base 11 of the measurement apparatus 10 as shown in part (1) of FIG. 5. At this time, the user bares the user's feet and puts the user's feet such that the left foot comes into contact with both of the left current supplying electrode 12*a* and the left voltage measuring electrode 12*b* and the right foot comes into contact with both of the right current supplying electrode 12*a* and the right voltage measuring electrode 12*b*.

Next, the user stands up from a state where the user sits on the chair as shown in part (2) of FIG. 5. At this time, the user maintains a state where the left foot comes into contact with both of the left current supplying electrode 12*a* and the left voltage measuring electrode 12*b* and the right foot comes into contact with both of the right current supplying electrode 12*a* and the right voltage measuring electrode 12*b*.

Further, the user stands on the measurement base 11 and waits until the stagger of the body is removed and the body becomes stable as shown in part (3) of FIG. 5. At this time, the user maintains a state where the left foot comes into contact with both of the left current supplying electrode 12*a* and the left voltage measuring electrode 12*b* and the right foot comes into contact with both of the right current supplying electrode 12*a* and the right voltage measuring electrode 12*b*.

In this way, while the user performs a standing-up motion, the load calculation unit 291 obtains the load on the measurement base 11 and the position of the center of gravity in the measurement base 11 based on the load measured by the load sensor 14. Further, the bioelectrical impedance measurement circuit 13 obtains a bioelectrical impedance (impedance Z, a resistance component R and a reactance component X of the impedance Z) based on the current between the right and left current supplying electrodes 12*a* and the potential difference (voltage) between the right and left voltage measuring electrodes 12*b*.

Figure 6:
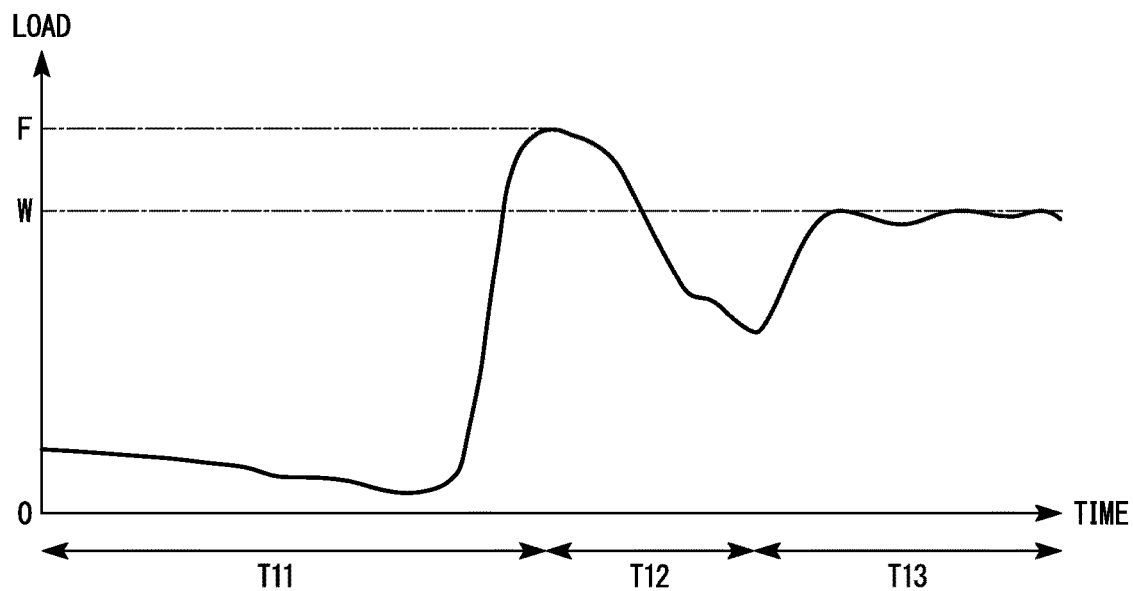
FIG. 6 is a graph showing an example of a load calculated by the load calculation unit in the embodiment.

FIG. 6 is a graph showing an example of a load calculated by the load calculation unit 291. The horizontal axis in FIG. 6 represents time, and the vertical axis represents load.

Further, F in FIG. 6 represents a maximum of the load calculated by the load calculation unit 291 in a series of motion, w represents the body weight of the user, and 0 represents a value when there is nothing on the measurement base.

In the interval of time T11, as shown in part (1) of FIG. 5, when the user stands up from a state where the user sits on the chair, first, since the load is transferred to the hip and the chair supports the load, the load calculated by the load calculation unit 291 is once decreased. Then, the load on the chair due to the hip is decreased, and the load calculated by the load calculation unit 291 increases. The load calculated by the load calculation unit 291 is maximized approximately at a time when the hip is separated from the chair.

The interval of time T12 represents a state during the user is standing up from the chair as shown in part (2) of FIG. 5, and after the load increases relative to the load in time T11, the load calculated by the load calculation unit 291 is decreased.

In the interval of time T13, when the user becomes a state where the user stands up, the load calculated by the load calculation unit 291 converges to a body weight w of the user as shown in part (3) of FIG. 5.

After step S102 of FIG. 4, the change information acquisition unit 293 acquires a muscle strength indicator, a muscle power indicator, a muscle quality indicator, and a muscle quantity indicator, based on the load and the bioelectrical impedance obtained in step S102 (step S103).

The changes in muscle strength, muscle power, muscle quality, and muscle quantity are described with reference to FIG. 7.

Figure 7:
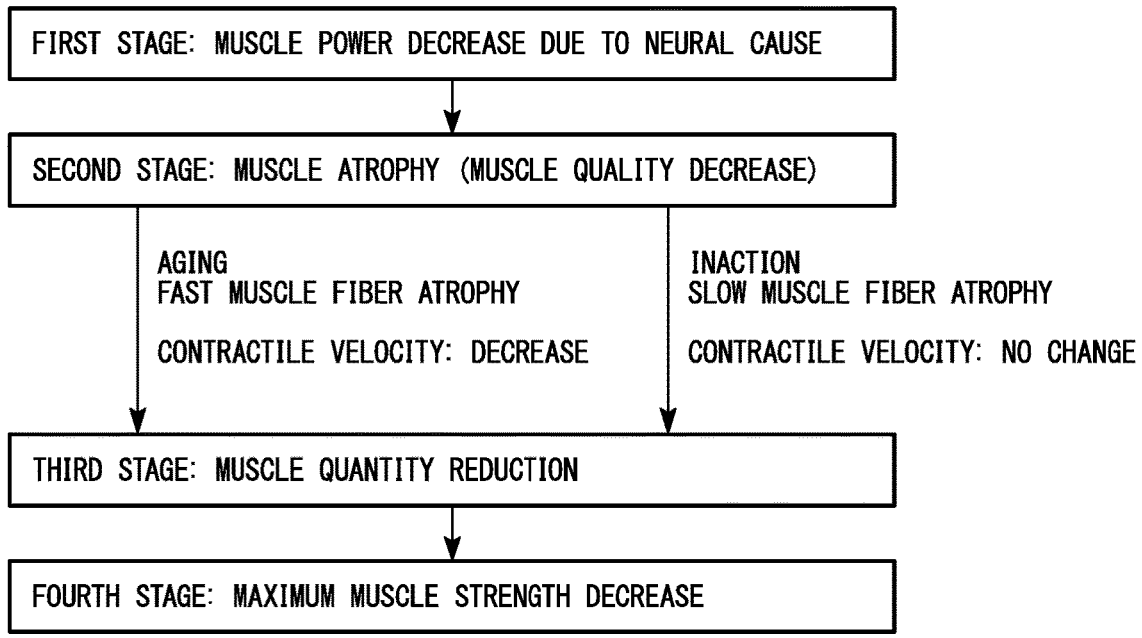
FIG. 7 is a view showing an example of the change process of a muscle condition.

FIG. 7 is a view showing an example of a process in which a muscle decays.

As a first stage when a muscle decays, a muscle power decreases due to a neural cause. Specifically, commands such as contraction to the muscle are not easily transmitted to the muscle, and the muscle power decreases.

Next, as a second stage, muscle atrophy occurs, and muscle quality decreases. At that time, the muscle that atrophies is different between aging and "inaction". Here, "inaction" represents not exercising or lack of exercise.

In case of aging, a fast muscle fiber atrophies. In this case, the contractile velocity of muscle decreases. On the other hand, in case of inaction, a slow muscle fiber atrophies. In this case, the contractile velocity of muscle does not decrease.

Next, as a third stage, muscle quantity is reduced.

Then, as a fourth stage, maximum muscle strength (muscle power) decreases.

In this way, in view of changes in muscle strength, muscle power, muscle quality, and muscle quantity, it is understood that in which stage in the process of change in the muscle stage shown in FIG. 7 the stage of decay of the muscle is, and a treatment corresponding to the stage can be performed. Therefore, the change information acquisition unit 293 calculates the change rate of each of the muscle strength indicator, the muscle power indicator, the muscle quality indicator, and the muscle quantity indicator as described above.

(Acquisition of Muscle Strength Indicator)

The change information acquisition unit 293 calculates a maximum body weight ratio F/w obtained by dividing a maximum F of the load calculated by the load calculation unit 291 in step S102 of FIG. 4 by the body weight w of the user as a muscle strength indicator. The muscle strength indicator acquired by the change information acquisition unit 293 is not limited to the maximum body weight ratio F/w. For example, the change information acquisition unit 293 may calculate a value obtained by dividing the difference between the maximum of the load and the minimum of the load by the body weight of the user as the muscle strength indicator. Alternatively, the change information acquisition unit 293 may acquire the measurement value of grip strength by using a grip dynamometer as a muscle strength indicator. Alternatively, the change information acquisition unit 293 may acquire the measurement value of muscle strength using a handheld dynamometer as a muscle strength indicator.

It is considered that a case where the change information acquisition unit 293 uses the maximum body weight ratio F/w as the muscle strength indicator is more accurate than a case where the change information acquisition unit 293 uses a value obtained by dividing the difference between the maximum of the load and the minimum of the load by the body weight of the user. This is because there is a possibility that it may be impossible to exactly specify the timing when the load is minimized.

When it is difficult to specify the maximum of the load, the change information acquisition unit 293 may detect the maximum of the load in a region from when the load is reduced to a predetermined load small threshold (for example, 20% of the body weight) or less to when the load first increases to a predetermined load large threshold (for example, 105% of the body weight) or more.

(Acquisition of Muscle Power Indicator)

The change information acquisition unit 293 calculates a maximum change rate body weight ratio RFD/w obtained by dividing a maximum RFD of the load change rate calculated by the load calculation unit 291 in step S102 of FIG. 4 by the body weight w of the user as a muscle power indicator.

Figure 8:
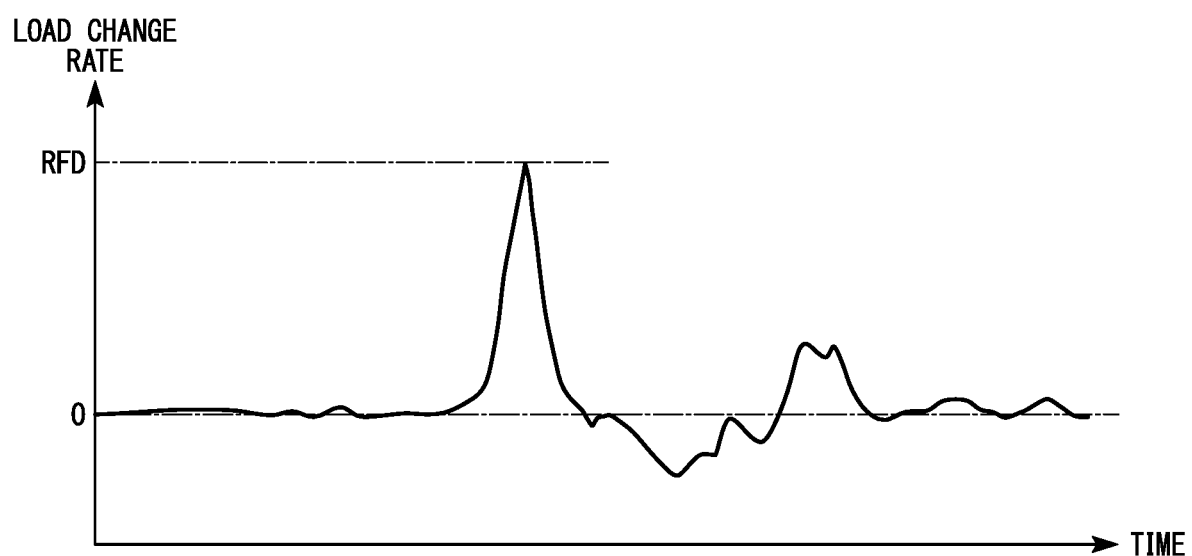
FIG. 8 is a graph showing an example of a load change rate in the embodiment.

FIG. 8 is a graph showing an example of a load change rate. The horizontal axis in FIG. 8 represents time, and the vertical axis represents load change rate. When the change rate is greater than 0, the load increases. On the other hand, when the change rate is smaller than 0, the load decreases. RFD in FIG. 8 represents a maximum of load change rate.

The muscle power indicator acquired by the change information acquisition unit 293 is not limited to the maximum change rate body weight ratio RFD/w. For example, the change information acquisition unit 293 may acquire a measurement value obtained by performing an isokinetic muscle strength measurement while changing a motion speed as the muscle power indicator. Alternatively, the change information acquisition unit 293 may acquire a measurement value of a vertical jump result or a measurement value of a standing broad jump result as the muscle power indicator.

(Acquisition of Muscle Quality Indicator)

The change information acquisition unit 293 calculates a muscle quality indicator, based on the bioelectrical impedance measured by the bioelectrical impedance measurement circuit 13 in step S102 of FIG. 4. For example, the change information acquisition unit 293 calculates R/X obtained by dividing the resistance component R in the bioelectrical impedance by the reactance component X as a muscle quality indicator.

The muscle quality indicator acquired by the change information acquisition unit 293 is not limited to R/X. For example, the change information acquisition unit 293 may calculate the ratio of impedance Zhigh at high frequency and impedance Zlow at low frequency as the muscle quality indicator. Further, for example, the change information acquisition unit 293 may calculate a value obtained by dividing impedance Zlow at 5 kHz by impedance Zhigh at 250 kHz as the muscle quality indicator.

(Acquisition of Muscle Quantity Indicator)

The change information acquisition unit 293 calculates a muscle quantity indicator based on the bioelectrical impedance measured by the bioelectrical impedance measurement circuit 13 in step S102 of FIG. 4. For example, the change information acquisition unit 293 calculates the muscle quantity by using the bioelectrical impedance, body weight, body height, age, sex, and the like and divides the calculated muscle quantity by the square of the user's body height ($Ht^2$). Dividing the muscle quantity by the square of the user's body height as the muscle quantity indicator is performed to exclude or reduce the effect of the body height since there is a relationship between the body height and the muscle quantity. The muscle quantity indicator obtained by dividing the muscle quantity by the square of the user's body height is represented as "muscle quantity/$Ht^2$".

The muscle quantity indicator acquired by the change information acquisition unit 293 is not limited to muscle quantity/$Ht^2$. For example, the change information acquisition unit 293 may calculate a value (four limbs muscle quantity/$Ht^2$) obtained by dividing a four limbs muscle quantity by the square of the user's body height as the muscle quantity indicator. Alternatively, the change information acquisition unit 293 may calculate a value (lower limb muscle quantity/$Ht^2$) obtained by dividing a lower limb muscle quantity by the square of the user's body height as the muscle quantity indicator. The change information acquisition unit 293 may calculate a value (lower limb muscle quantity/w) obtained by dividing a lower limb muscle quantity by the user's body weight w as the muscle quantity indicator.

The estimated energy requirement calculation unit 294 calculates an estimated energy requirement after step S102 of FIG. 4 (step S104).

Specifically, the estimated energy requirement calculation unit 294 calculates a value obtained by multiplying a basal metabolism quantity by a coefficient of body activity level as the estimated energy requirement. For example, the estimated energy requirement calculation unit 294 stores in advance a basal metabolism quantity in association with an age, sex, and body weight and reads out a basal metabolism quantity associated with the age, sex, and body weight of the user. The estimated energy requirement calculation unit 294 classifies the body activity level into three stages of high, middle, and low based on a reply to a questionnaire to the user and reads out a coefficient stored in advance for each level depending on the age.

Then, the estimated energy requirement calculation unit 294 multiplies the obtained basal metabolism quantity by the coefficient to calculate the estimated energy requirement.

After step S103 and step S104, the type determination unit 295 performs a type determination of the change in a muscle condition of a user (step S105).

FIG. 9 is a view showing an example of a process sequence of a type determination of the change in a muscle condition of a user performed by the type determination unit 295. FIG. 9 shows an example of a process sequence of a type determination of the change in a muscle condition used for general people.

In FIG. 9, the type determination unit 295 determines whether or not the change rate of muscle strength indicator Δ % F/w is smaller than 0, that is, whether or not muscle strength is reduced (step S201). F/w is a value obtained by dividing muscle strength F by body weight w and corresponds to an example of muscle strength indicator. Further, "Δ %" represents a change rate. For example, Δ % F/w represents the change rate of F/w.

When it is determined that Δ % F/w is smaller than 0 in step S201 (step S201: Yes), the type determination unit 295 determines whether or not the change rate Δ % RFD/w of muscle power indicator is smaller than 0, that is, whether or not muscle power decreases (step S202).

When it is determined that Δ % RFD/w is smaller than 0 in step S202 (step S202: Yes), the type determination unit 295 determines whether or not the change rate Δ % R/X of muscle quality indicator R/X is smaller than 0, that is, whether or not muscle atrophy is occurring (step S203).

When it is determined that Δ % R/X is smaller than 0 in step S203 (step S203: Yes), the type determination unit 295 determines whether or not the change rate "Δ % muscle quantity/$Ht^2$" of muscle quantity indicator is smaller than 0, that is, whether or not muscle quantity is reduced (step S204).

When it is determined that "Δ % muscle quantity/$Ht^2$" is smaller than 0 in step S204 (step S204: Yes), the type determination unit 295 determines that the type of change in the muscle condition is A: quick motion decrease type (step S205). That is, type A (quick motion decrease type) represents a category considered to be one in which there is a high possibility that a fast muscle fiber atrophies.

On the other hand, when it is determined that the change rate of "Δ % muscle quantity/$Ht^2$" is 0 or more in step S204 (step S204: No), the type determination unit 295 determines that the type of change in the muscle condition is B: quick motion decrease caution type (step S206). That is, type B (quick motion decrease caution type) represents a category considered to be one in which although there is a possibility that a fast muscle fiber atrophies similarly to type A, there is a low possibility of atrophy, or the degree of atrophy is light, compared to the case of type A.

On the other hand, when it is determined that Δ % R/X is 0 or more in step S203 (step S203: No), the type determination unit 295 determines that the type of change in the muscle condition is C: muscle strength and muscle power decrease type due to a neural cause (step S207). That is, type C (muscle strength and muscle power decrease type due to a neural cause) represents a category considered to be one in which there is a high possibility that muscle fiber atrophy will occur in the future.

On the other hand, when it is determined that Δ % RFD/w is 0 or more in step S202 (step S202: No), the type determination unit 295 determines whether or not the change rate Δ % R/X of muscle quality indicator is smaller than 0, that is, whether or not muscle atrophy is occurring (step S208).

When it is determined that Δ % R/X is smaller than 0 in step S208 (step S208: Yes), the type determination unit 295 determines whether or not the change rate of muscle quantity indicator is smaller than 0, that is, whether or not muscle quantity is reduced (step S209).

When it is determined that "Δ % muscle quantity/$Ht^2$" is smaller than 0 in step S209 (step S209: Yes), the type determination unit 295 determines that the type of change in the muscle condition is D: motion persistence decrease type (step S210). That is, type D (motion persistence decrease type) represents a category considered to be one in which there is a high possibility that a slow muscle fiber atrophies.

On the other hand, when it is determined that "Δ % muscle quantity/$Ht^2$" is 0 or more in step S209 (step S209: No), the type determination unit 295 determines that the type of change in the muscle condition is E: motion persistence decrease caution type (step S211). That is, type E (motion persistence decrease caution type) represents a category considered to be one in which although there is a possibility that a slow muscle fiber atrophies similarly to type D, there is a lower possibility of atrophy, or the degree of atrophy is lighter, compared to the case of type D.

On the other hand, when it is determined that Δ % R/X is 0 or more in step S208 (step S208: No), the type determination unit 295 determines that the type of change in the muscle condition is F: muscle strength decrease type (step S212). That is, type F represents a category considered to be one in which muscle strength decreases.

On the other hand, when it is determined that Δ % F/w is 0 or more in step S201 (step S201: No), the routine proceeds to step S221 of FIG. 10.

FIG. 10 is a view showing an example of a process sequence of a type determination of the change in a muscle condition of a user performed by the type determination unit 295 when it is determined that Δ % F/w is 0 or more, that is, when it is determined that muscle strength is not reduced. In FIG. 10, the type determination unit 295 determines whether the change rate Δ % RFD/w of muscle power indicator is smaller than 0, that is, whether or not muscle power decreases (step S221).

When it is determined that Δ % RFD/w is smaller than 0 in step S221 (step S221: Yes), the type determination unit 295 determines whether or not the change rate Δ % R/X of muscle quality indicator is smaller than 0, that is, whether or not muscle atrophy is occurring (step S222).

When it is determined that Δ % R/X is smaller than 0 in step S222 (step S222: Yes), the type determination unit 295 determines whether or not the change rate of muscle quantity indicator is smaller than 0, that is, whether or not muscle quantity is reduced (step S223).

When it is determined that "Δ % muscle quantity/Ht$^2$" is smaller than 0 in step S223 (step S223: Yes), the type determination unit 295 determines that the type of change in the muscle condition is G: quick motion decrease type (step S224). That is, type G represents a category considered to be one in which although type G is similar to type A in that there is a high possibility that a fast muscle fiber atrophies, type G is different from type A in suggestion of meal behavior.

On the other hand, when it is determined that "Δ % muscle quantity/Ht$^2$" is 0 or more in step S223 (step S223: No), the type determination unit 295 determines that the type of change in the muscle condition is H: quick motion decrease caution type (step S225). That is, type H represents a category considered to be one in which although type H is similar to type B in that there is a possibility that a fast muscle fiber atrophies, type H is different from type B in suggestion of meal behavior.

On the other hand, when it is determined that Δ % R/X is 0 or more in step S222 (step S222: No), the type determination unit 295 determines that the type of change in the muscle condition is I: muscle strength and muscle power decrease type due to a neural cause (step S226). That is, type I represents a category considered to be one in which although type I is similar to type C in that the cause of change in the muscle condition is considered to be a neural one and that there is a high possibility that muscle fiber atrophy will occur in the future, type I is different from type C in suggestion of meal behavior.

On the other hand, when it is determined that Δ % RFD/w is 0 or more in step S221 (step S221: No), the type determination unit 295 determines whether or not the change rate Δ % R/X of muscle quality indicator is smaller than 0, that is, whether or not muscle atrophy is occurring (step S227).

When it is determined that Δ % R/X is smaller than 0 in step S227 (step S227: Yes), the type determination unit 295 determines whether or not the change rate of muscle quantity indicator is smaller than 0, that is, whether or not muscle quantity is reduced (step S228).

When it is determined that "Δ % muscle quantity/Ht$^2$" is smaller than 0 in step S228 (step S228: Yes), the type determination unit 295 determines that the type of change in the muscle condition is J: muscle atrophy type (step S229). That is, type J represents a category considered to be one in which muscle atrophy is occurring.

On the other hand, when it is determined that "Δ % muscle quantity/Ht$^2$" is 0 or more in step S228 (step S228: No), the type determination unit 295 determines that the type of change in the muscle condition is K: fatty infiltration type (step S230). That is, type K (fatty infiltration type) represents a category considered to be one in which fat infiltrates muscle.

On the other hand, when it is determined that Δ % R/X is 0 or more in step S227 (step S227: No), the type determination unit 295 determines whether or not the change rate of muscle quantity indicator is smaller than 0, that is, whether or not muscle quantity is reduced (step S231).

When it is determined that "Δ % muscle quantity/Ht$^2$" is smaller than 0 in step S231 (step S231: Yes), the type determination unit 295 determines that the type of change in the muscle condition is L: muscle quantity reduction type (step S232). That is, type L represents a category considered to be one in which muscle quantity decreases.

On the other hand, when it is determined that "Δ % muscle quantity/Ht$^2$" is 0 or more in step S231 (step S231: No), the type determination unit 295 determines that the type of change in the muscle condition is M: no problem (step S233). That is, type M represents a category considered to be one in which no problem occurs in the muscle condition.

In this way, the type determination unit 295 classifies the change in the muscle condition into any of thirteen types from type A to type M.

The type name is not limited to those shown in FIG. 9 and FIG. 10.

Figure 11:
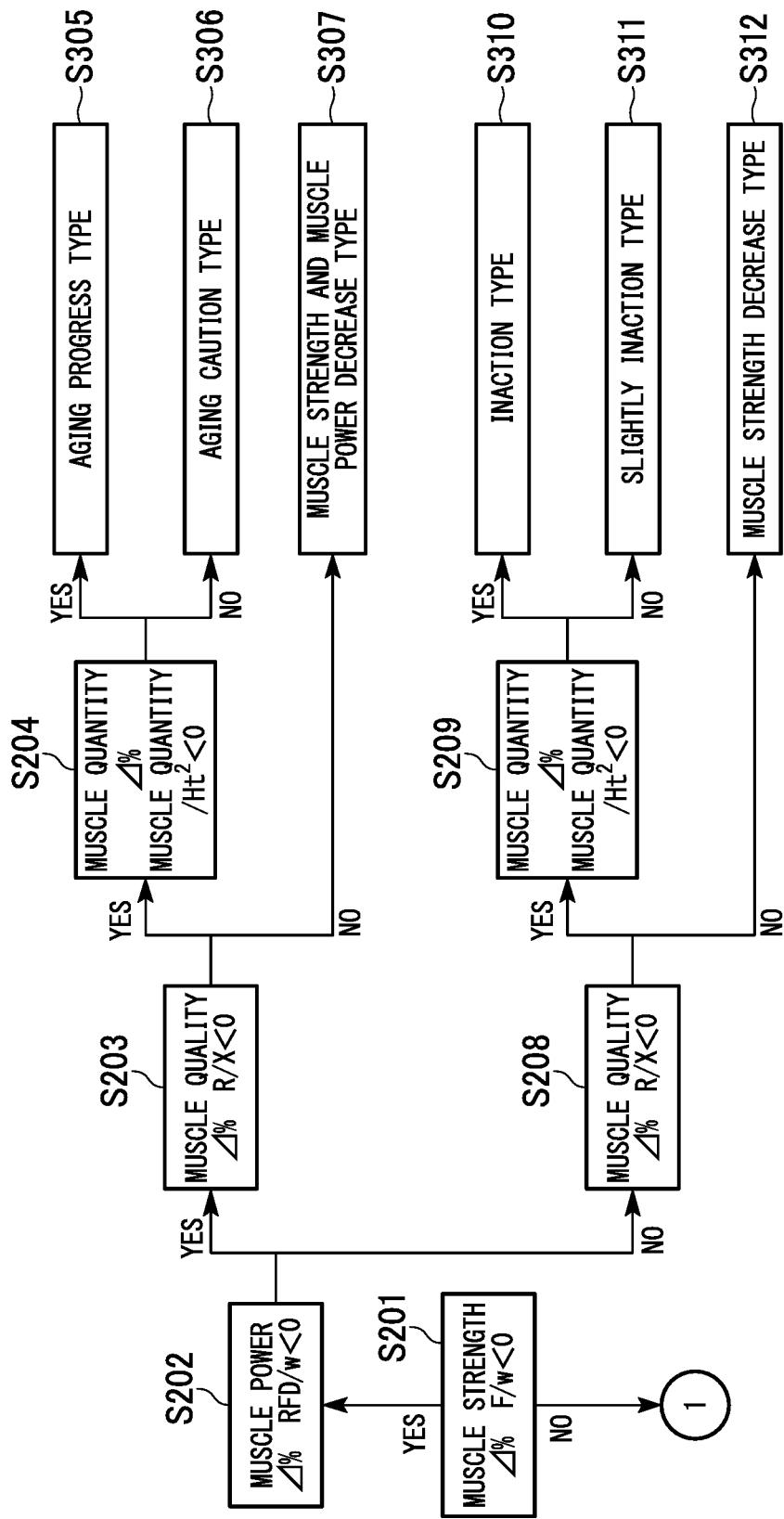
FIG. 11 is a view showing an example of a process sequence of a type determination of the change in a muscle condition of a user performed by the type determination unit when another type name is given in the embodiment.

FIG. 11 is a view showing an example of a process sequence of a type determination of the change in a muscle condition of a user, performed by the type determination unit 295 when another type name is given. FIG. 9 shows an example of a process sequence of a type determination of the change in a muscle condition used for general people. On the other hand, FIG. 11 shows an example of a process sequence of a type determination of the change in a muscle condition used for elderly people. FIG. 11 corresponds to FIG. 9. Diagrammatic representation and a description are omitted; however, the type determination unit 295 also performs a process of a type determination of the change in a muscle condition for elderly people corresponding to FIG. 10, similarly to the process of FIG. 11 corresponding to FIG. 9.

The processes from step S201 to step S209 of FIG. 11 are similar to the processes from step S201 to step S209 of FIG. 9. The similar processes are given by the same reference numerals, and a description of similar processes is omitted.

On the other hand, in FIG. 11, type names are different from those of FIG. 9.

In step S305 of FIG. 11 corresponding to step S205 of FIG. 9, the type determination unit 295 determines that the type of change in the muscle condition is an aging progress type. The aging progress type represents a category considered to be one in which there is a high possibility that aging of the muscle condition progresses and a fast muscle fiber atrophies.

In step S306 of FIG. 11 corresponding to step S206 of FIG. 9, the type determination unit 295 determines that the type of change in the muscle condition is an aging caution type. That is, the aging caution type represents a category considered to be one in which there is a lower possibility of atrophy of a fast muscle fiber, or caution is required for aging of the muscle condition although the degree of atrophy is lighter, compared to the case of the aging progress type.

In step S307 of FIG. 11 corresponding to step S207 of FIG. 9, the type determination unit 295 determines that the type of change in the muscle condition is a muscle strength and muscle power decrease type. That is, the muscle strength and muscle power decrease type represents a category considered to be one in which muscle strength and muscle power decrease.

In step S310 of FIG. 11 corresponding to step S210 of FIG. 9, the type determination unit 295 determines that the type of change in the muscle condition is an inaction type. That is, the inaction type represents a category considered to be one in which there is a high possibility that a slow muscle fiber atrophies due to lack of exercise.

In step S311 of FIG. 11 corresponding to step S211 of FIG. 9, the type determination unit 295 determines that the type of change in the muscle condition is a slightly inaction type. That is, the slightly inaction type represents a category considered to be one in which there is a lower possibility of atrophy of a slow muscle fiber, or caution is required for lack of exercise although the degree of atrophy is lighter, compared to the case of the inaction type.

In step S312 of FIG. 11 corresponding to step S212 of FIG. 9, the type determination unit 295 determines that the type of change in the muscle condition is a muscle strength decrease type. That is, the muscle strength decrease type represents a category considered to be one in which muscle strength decreases.

In this way, the type name of the change in the muscle condition is not limited to those shown in FIG. 9 and FIG. 10.

After step S105 of FIG. 4, the type determination unit 295 determines the degree of aging muscle (step S106).

Figure 12:
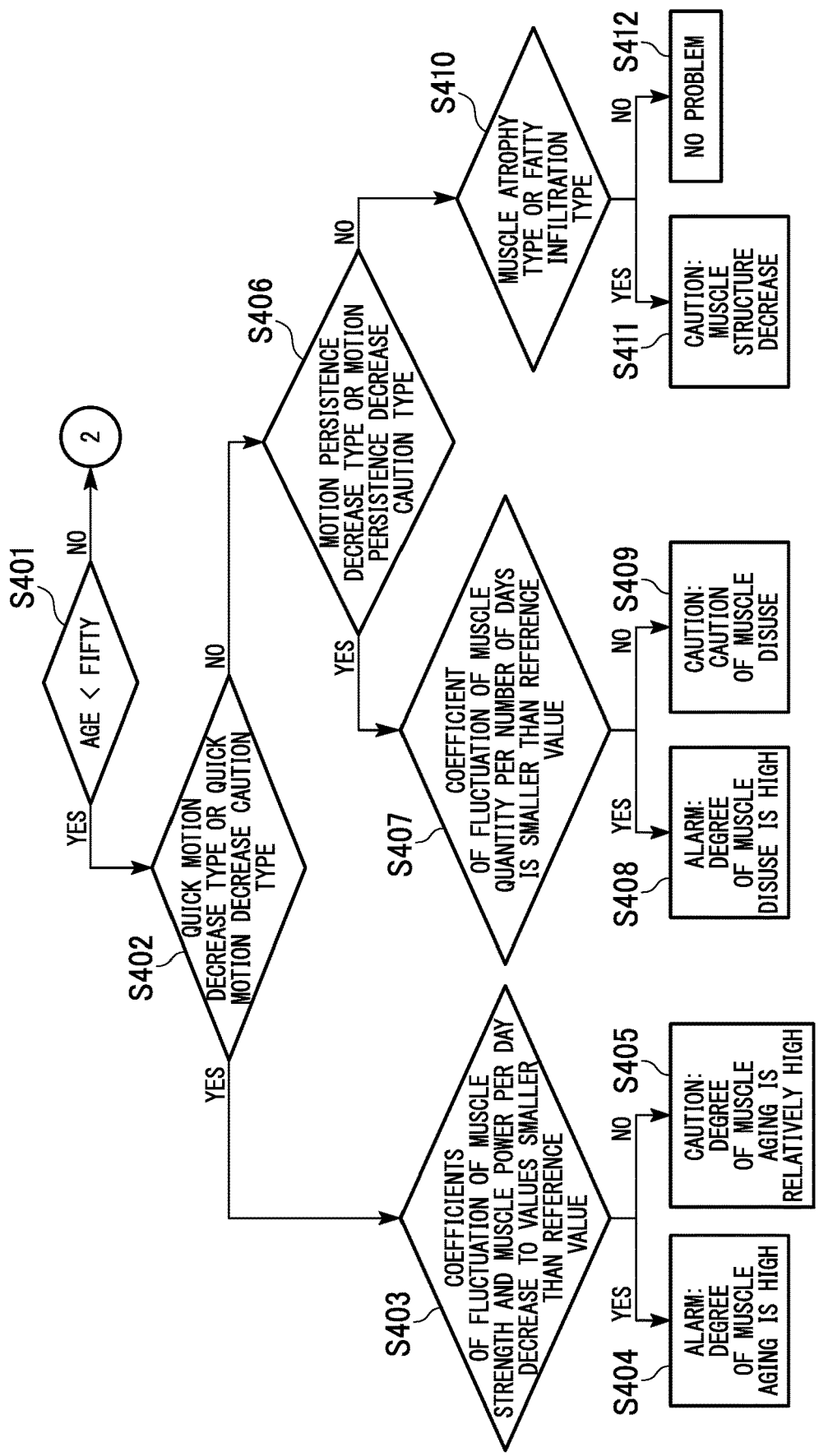
FIG. 12 is a view showing an example of a process sequence of evaluation depending on the age for the change in a muscle condition of a user performed by the type determination unit in the embodiment.

FIG. 12 is a view showing an example of a process sequence of evaluation depending on the age for a muscle condition of a user, performed by the type determination unit 295. The type determination unit 295 performs a process of FIG. 12 in step S106 of FIG. 4.

In FIG. 12, the type determination unit 295 determines whether or not the age of the user is less than fifty (step S401).

When it is determined that the age of the user is less than fifty in step S401 (step S401: YES), the type determination unit 295 determines whether or not the type determined in step S105 of FIG. 4 is the quick motion decrease type (type A) or the quick motion decrease caution type (type B) (step S402).

When it is determined that the type determined in step S105 of FIG. 4 is the quick motion decrease type or the quick motion decrease caution type in step S402 (step S402: Yes), the type determination unit 295 determines whether or not a coefficient of fluctuation (that is, a value obtained by dividing a coefficient of fluctuation of muscle strength by the number of days) per day of muscle strength represents a muscle strength decrease to a value which is smaller than a reference value (for example, decrease by 0.0022 percent) or whether or not a coefficient of fluctuation (that is, a value obtained by dividing a coefficient of fluctuation of muscle power by the number of days) per day of muscle power represents a muscle power decrease to a value which is smaller than a reference value (step S403).

The coefficient of fluctuation per day is represented by Expression (1).

$$\text{coefficient of fluctuation per day} = \{(\text{current measurement value} - \text{past value})/\text{past value} \times 100(\%)\}/\text{the number of days from the day when the past value is measured to the day when the current measurement value is measured} \quad (1)$$

When it is determined that both coefficients of fluctuation represent a decrease to a value which is smaller than the reference value in step S403 (step S403: Yes), the type determination unit 295 determines that evaluation of the muscle condition corresponds to an alarm that the degree of muscle aging is high (step S404). In this case, the determination result in step S402 represents aging muscle, and the determination result in step S403 represents an abrupt change of muscle condition. Therefore, the type determination unit 295 determines that special caution is required for aging muscle.

On the other hand, when it is determined that at least one of the coefficients of fluctuation does not represent a decrease to a value which is smaller than the reference value in step S403 (step S403: No), the type determination unit 295 determines that evaluation of the muscle condition corresponds to a caution that the degree of muscle aging is relatively high (step S405). In this case, the determination result in step S402 represents aging muscle, and on the other hand, the determination result in step S403 represents that the change of the muscle condition is not abrupt. Therefore, the type determination unit 295 determines that caution is required for aging muscle.

On the other hand, when it is determined that the type determined in step S105 of FIG. 4 is neither the quick motion decrease type nor the quick motion decrease caution type in step S402 (step S402: No), the type determination unit 295 determines whether or not the type determined in step S105 of FIG. 4 is the motion persistence decrease type (type D) or the motion persistence decrease caution type (type E) (step S406).

When it is determined that the type determined in step S105 of FIG. 4 is the motion persistence decrease type or the motion persistence decrease caution type in step S406 (step S406: Yes), the type determination unit 295 determines whether or not a coefficient of fluctuation per day of muscle quantity represents a muscle quantity decrease to a value which is smaller than a reference value (for example, decrease by 0.0022 percent) (step S407).

When it is determined that the coefficient of fluctuation per day of muscle quantity represents a decrease to a value which is smaller than the reference value in step S407 (step S407: Yes), the type determination unit 295 determines that evaluation of the muscle condition corresponds to an alarm that the degree of muscle disuse is high (step S408). In this case, the determination result in step S406 represents that muscle is not used, and the determination result in step S407 represents an abrupt change of muscle condition. Therefore, the type determination unit 295 determines that special caution is required due to muscle disuse.

On the other hand, when it is determined that the coefficient of fluctuation per day of muscle quantity does not represent a decrease to a value which is smaller than the reference value in step S407 (step S407: No), the type determination unit 295 determines that evaluation of the muscle condition corresponds to a caution that the degree of muscle disuse is relatively high (step S409). In this case, the determination result in step S406 represents that muscle is not used, and on the other hand, the determination result in step S403 represents that the change of the muscle condition is not abrupt. Therefore, the type determination unit 295 determines that caution is required due to muscle disuse.

On the other hand, when it is determined that the type determined in step S105 of FIG. 4 is neither the motion persistence decrease type nor the motion persistence decrease caution type in step S406 (step S406: No), the type determination unit 295 determines whether or not the type determined in step S105 of FIG. 4 is the muscle atrophy type or the fatty infiltration type (step S410).

When it is determined that the type determined in step S105 of FIG. 4 is the muscle atrophy type or the fatty infiltration type in step S410 (step S410: Yes), the type determination unit 295 determines that evaluation of the muscle condition corresponds to a caution toward a muscle structure decrease (step S411).

On the other hand, when it is determined that the type determined in step S105 of FIG. 4 is neither the muscle atrophy type nor the fatty infiltration type in step S410 (step S410: No), the type determination unit 295 determines that evaluation of the muscle condition corresponds to no problem (step S412).

On the other hand, when it is determined that the age of the user is fifty or more in step S401 (step S401: NO), the routine proceeds to step S421 of FIG. 13.

Figure 13:
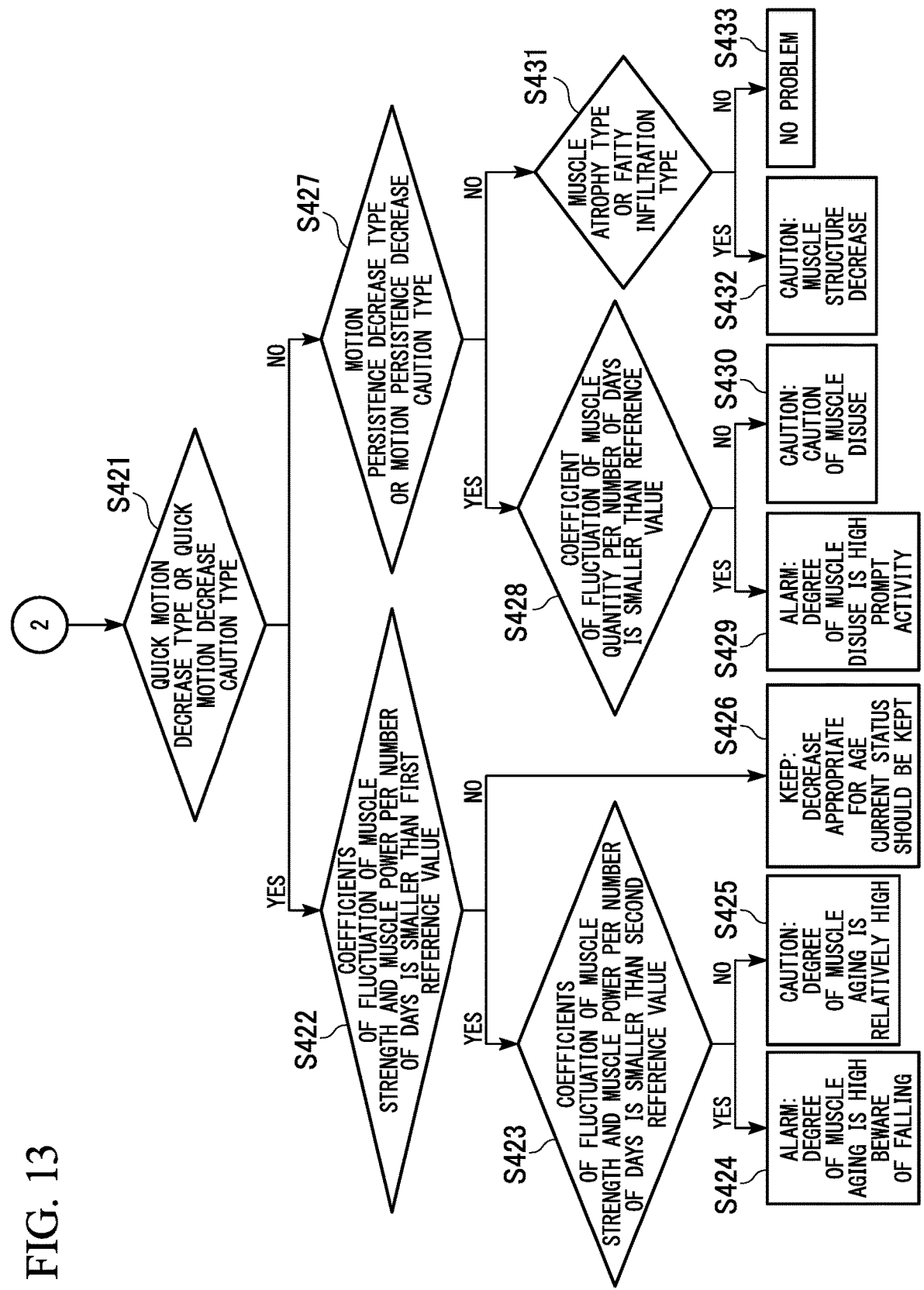
FIG. 13 is a view showing an example of a process sequence of evaluation depending on the age for the change in a muscle condition of a user performed by the type determination unit in the embodiment.

FIG. 13 is a view showing an example of a process sequence of evaluation depending on the age for a muscle condition of a user, performed by the type determination unit 295 when it is determined that the age of the user is fifty or more. In FIG. 13, the type determination unit 295 determines whether or not the type determined in step S105 of FIG. 4 is the quick motion decrease type (type A) or the quick motion decrease caution type (type B) (step S421).

When it is determined that the type determined in step S105 of FIG. 4 is the quick motion decrease type or the quick motion decrease caution type in step S421 (step S421: Yes), the type determination unit 295 determines whether or not a coefficient of fluctuation per day of muscle strength represents a muscle strength decrease to a value which is smaller than a first reference value (for example, decrease by 0.0022 percent) and whether or not a coefficient of fluctuation per day of muscle power represents a muscle power decrease to a value which is smaller than a first reference value (step S422).

When it is determined that both coefficients of fluctuation represent a decrease to a value which is smaller than the first reference value in step S422 (step S422: Yes), the type determination unit 295 determines whether or not a coefficient of fluctuation per day of muscle strength represents a muscle strength decrease to a value which is smaller than a second reference value (for example, decrease by 0.0036 percent) and whether or not a coefficient of fluctuation per day of muscle power represents a muscle power decrease to a value which is smaller than the second reference value (step S423).

Any of or both of the first reference value and the second reference value may be capable of being set and changed by an administrator. Another reference value may be capable of being set and changed by an administrator.

When it is determined that both coefficients of fluctuation represent a decrease to a value which is smaller than the second reference value in step S423 (step S423: Yes), the type determination unit 295 determines that evaluation of the muscle condition corresponds to an alarm that the degree of muscle aging is high and beware of falling (step S424). In this case, the determination result in step S421 represents aging muscle, and the determination result in step S422 and step S423 represents an abrupt change of muscle condition. Therefore, the type determination unit 295 determines that special caution is required for aging muscle.

On the other hand, when it is determined that at least one of the coefficients of fluctuation does not represent a decrease to a value which is smaller than the second reference value in step S423 (step S423: No), the type determination unit 295 determines that evaluation of the muscle condition corresponds to a caution that the degree of muscle aging is relatively high (step S425). In this case, the determination result in step S421 represents aging muscle, and on the other hand, the determination result in step S422 represents an abrupt change of muscle condition. On the other hand, the determination result in step S423 represents that the change of the muscle condition is not abrupt compared to a case of step S424. Therefore, the type determination unit 295 determines that caution is required for aging muscle.

On the other hand, when it is determined that at least one of the coefficients of fluctuation does not represent a decrease to a value which is smaller than the first reference value in step S422 (step S422: No), the type determination unit 295 determines that evaluation of the muscle condition corresponds to that the decrease of muscle is appropriate for the age and the current status should be kept (step S426).

On the other hand, when it is determined that the type determined in step S105 of FIG. 4 is neither the quick motion decrease type nor the quick motion decrease caution type in step S421 (step S421: No), the type determination unit 295 determines whether or not the type determined in step S105 of FIG. 4 is the motion persistence decrease type (type D) or the motion persistence decrease caution type (type E) (step S427).

When it is determined that the type determined in step S105 of FIG. 4 is the motion persistence decrease type or the motion persistence decrease caution type in step S427 (step S427: Yes), the type determination unit 295 determines whether or not a coefficient of fluctuation per day of muscle quantity represents a muscle quantity decrease to a value which is smaller than a reference value (for example, decrease by 0.0022 percent) (step S428).

When it is determined that the coefficient of fluctuation per day of muscle quantity represents a decrease to a value which is smaller than the reference value in step S428 (step S428: Yes), the type determination unit 295 determines that evaluation of the muscle condition corresponds to an alarm that the degree of muscle disuse is high and it is necessary to prompt activity (step S429). In this case, the determination result in step S427 represents that muscle is not used, and the determination result in step S428 represents an abrupt change of muscle condition. Therefore, the type determination unit 295 determines that special caution is required due to muscle disuse.

On the other hand, when it is determined that the coefficient of fluctuation per day of muscle quantity does not represent a decrease to a value which is smaller than the reference value in step S428 (step S428: No), the type determination unit 295 determines that evaluation of the muscle condition corresponds to a caution that the degree of muscle disuse is relatively high (step S430). In this case, the determination result in step S427 represents that muscle is not used, and on the other hand, the determination result in step S428 represents that the change of the muscle condition is not abrupt. Therefore, the type determination unit 295 determines that caution is required due to muscle disuse.

On the other hand, when it is determined that the type determined in step S105 of FIG. 4 is neither the motion persistence decrease type nor the motion persistence decrease caution type in step S427 (step S427: No), the type determination unit 295 determines whether or not the type determined in step S105 of FIG. 4 is the muscle atrophy type or the fatty infiltration type (step S431).

When it is determined that the type determined in step S105 of FIG. 4 is the muscle atrophy type or the fatty infiltration type in step S431 (step S431: Yes), the type determination unit 295 determines that evaluation of the muscle condition corresponds to a caution toward a muscle structure decrease (step S432).

On the other hand, when it is determined that the type determined in step S105 of FIG. 4 is neither the muscle atrophy type nor the fatty infiltration type in step S431 (step S431: No), the type determination unit 295 determines that evaluation of the muscle condition corresponds to no problem (step S433).

In this way, the type determination unit 295 evaluates the muscle condition depending on whether the user's age is less than fifty or the user's age is fifty or more.

Further, after step S105 of FIG. 4, the treatment determination unit 296 suggests exercise behavior (step S107). For example, the treatment determination unit 296 stores in advance thirteen types in step S105 in association with exercises such as walking. Then, the treatment determination unit 296 reads out an exercise corresponding to a type determined by the type determination unit 295 in step S105 and presents the exercise which is read out to the user. Presentation of the exercise to the user is performed, for example, by the display unit 210 displaying the exercise.

Further, after step S105 of FIG. 4, the treatment determination unit 296 suggests meal behavior (step S108). For example, the treatment determination unit 296 stores in advance thirteen types in step S105 in association with ingredients and recipe ideas. Then, the treatment determination unit 296 reads out an ingredient and a recipe idea corresponding to a type determined by the type determination unit 295 in step S105 and presents the ingredient and the recipe idea which are read out to the user. This suggestion of nutrition behavior is described with reference to FIG. 14 to FIG. 17.

FIG. 14 is a view showing a relationship between a muscle condition and a category of required nutrition. Each row of FIG. 14 shows a muscle condition, a determination basis of the muscle condition, a cause and phenomenon of the muscle condition, and a category of required nutrition in case of the muscle condition, to be associated with each other.

For example, in the case of muscle strength decrease, the determination basis is "$\Delta$ % F/w<0" as shown in step S201 of FIG. 9. FIG. 9 shows "information transmission quantity decrease", "nerve degradation", "muscle fiber composition ratio degradation", and "many cells" as the cause and phenomenon of muscle strength decrease. FIG. 9 shows that nutrition for the brain is required in the case of muscle strength decrease.

Figure 15:
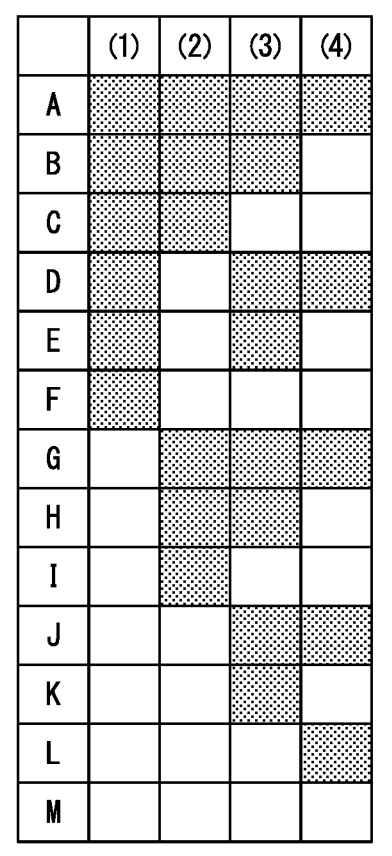

FIG. 15 is a view showing a relationship between thirteen types in step S105 of FIG. 4 and the category of nutrition shown in FIG. 14. The rows of FIG. 15 correspond to thirteen types of type A to type M, and the columns correspond to four nutrition: (1) nutrition for the brain, (2) muscle contraction (nutrition required at the time of muscle contraction), (3) muscle cell (nutrition required for adjusting muscle cells), and (4) muscle glycogen.

Whether or not nutrition is necessary is represented by the presence or absence of pattern. For example, in the case of type B (quick motion decrease caution type), the necessity of nutrition of the above (1), (2), and (3) is represented by the presence of pattern. On the other hand, the absence of pattern represents that nutrition (4) is not necessary as the treatment for type B.

FIG. 16 is a view of showing a relationship between the category of nutrition shown in FIG. 14 and FIG. 15 and a specific nutrition. Each row of FIG. 16 shows the category of nutrition and the specific nutrition to be associated with each other.

For example, FIG. 16 shows tryptophan (serotonine), phenylalanine, tyrosine (dopamine), GABA (γ-aminobutyric acid), and leucine as main nutrition regarding nutrition for the brain. Further, FIG. 16 shows vitamin B6, vitamin B2, and magnesium as metabolic nutrition that prompts ingestion of tryptophan (serotonine).

FIG. 17 is a view showing a relationship between nutrition and ingredients. Each row of FIG. 17 shows nutrition and an ingredient including the nutrition to be associated with each other. For example, FIG. 17 shows a banana, soymilk, milk, yogurt, and process cheese as an ingredient including tryptophan.

As shown in FIG. 14 to FIG. 17, a type of change in the muscle condition and an ingredient effective for the type can be associated with each other.

Therefore, the treatment determination unit 296 stores thirteen types (type A to type M) of muscle condition in association with an ingredient effective for each type and a recipe using the ingredient in advance.

Then, the treatment determination unit 296 reads out an ingredient and a recipe associated with a type selected by the type determination unit 295 in step S105 of FIG. 4 and presents the ingredient and the recipe which are read out to the user.

Alternatively, the treatment determination unit 296 stores thirteen types of muscle conditions and ingredients effective in the types in advance. Then, the treatment determination unit 296 may read out an ingredient associated with a type selected by the type determination unit 295 in step S105 of FIG. 4 to present the ingredient which is read out to the user and further search a recipe including the ingredient to present the searched recipe to the user. The treatment determination unit 296 searches a recipe, for example, via the Internet. Alternatively, the treatment determination unit 296 may search a recipe via other than the Internet; for example, the treatment determination unit 296 may search a recipe using a dedicated database.

Figure 18:
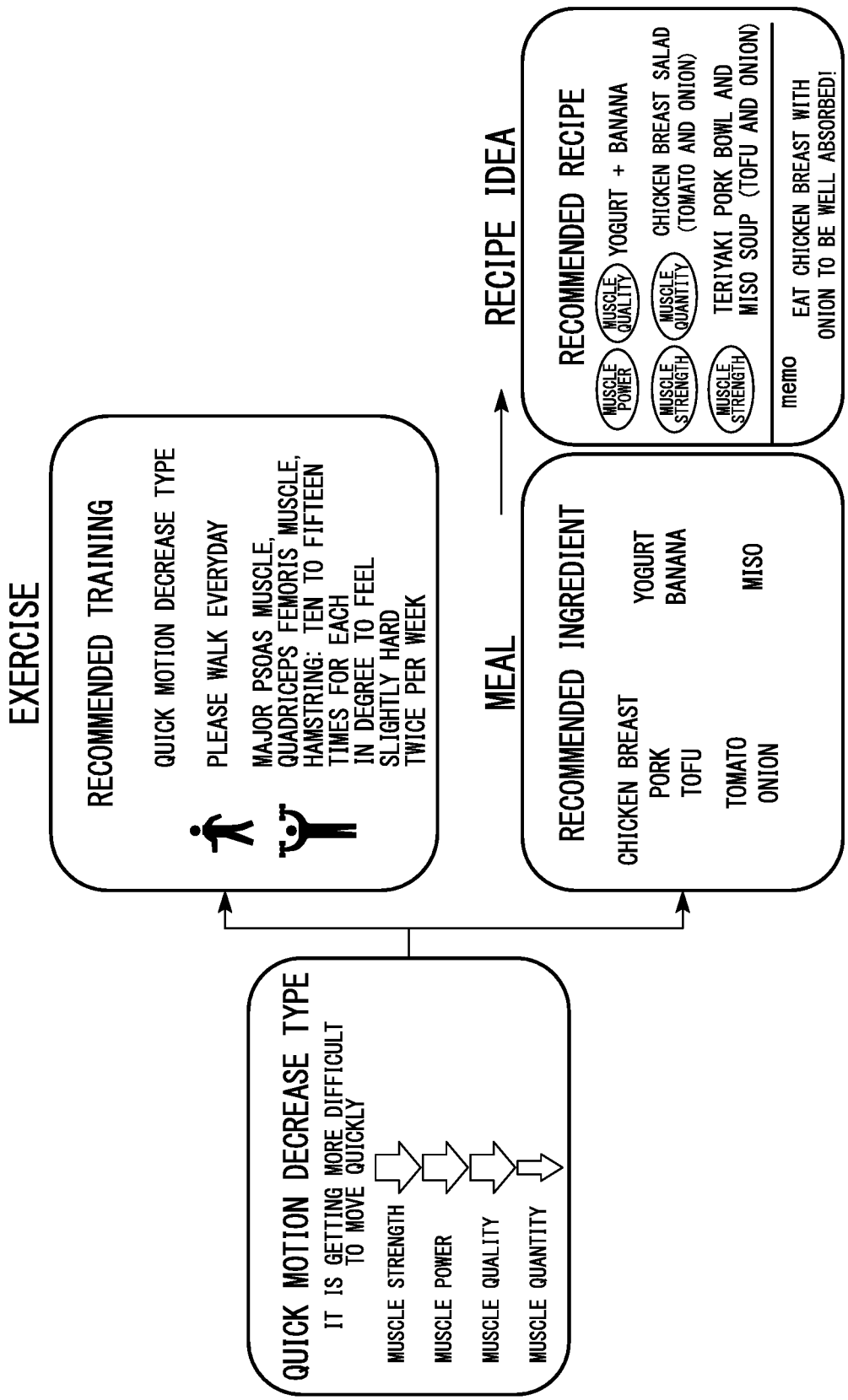
FIG. 18 is a view showing a first example of a display screen of the type of change in a muscle condition and a treatment, displayed by a display unit in the embodiment.

FIG. 18 is a view showing a first example of a display screen of the type of change in a muscle condition and a treatment, displayed by the display unit 210. FIG. 18 shows an example of a display screen in the case of the quick motion decrease type (type A).

FIG. 18 shows changes of muscle strength, muscle power, muscle quality, and muscle quantity with arrows in addition to type name "quick motion decrease type" as a display of type. A downward wide arrow indicates a large decrease rate, and a downward narrow arrow indicates a small decrease rate.

Further, FIG. 18 shows training effective for the quick motion decrease type as an exercise suggestion. FIG. 18 shows ingredients and recipes effective for the quick motion decrease type for breakfast, lunch, and dinner as a nutrition suggestion.

Figure 19:
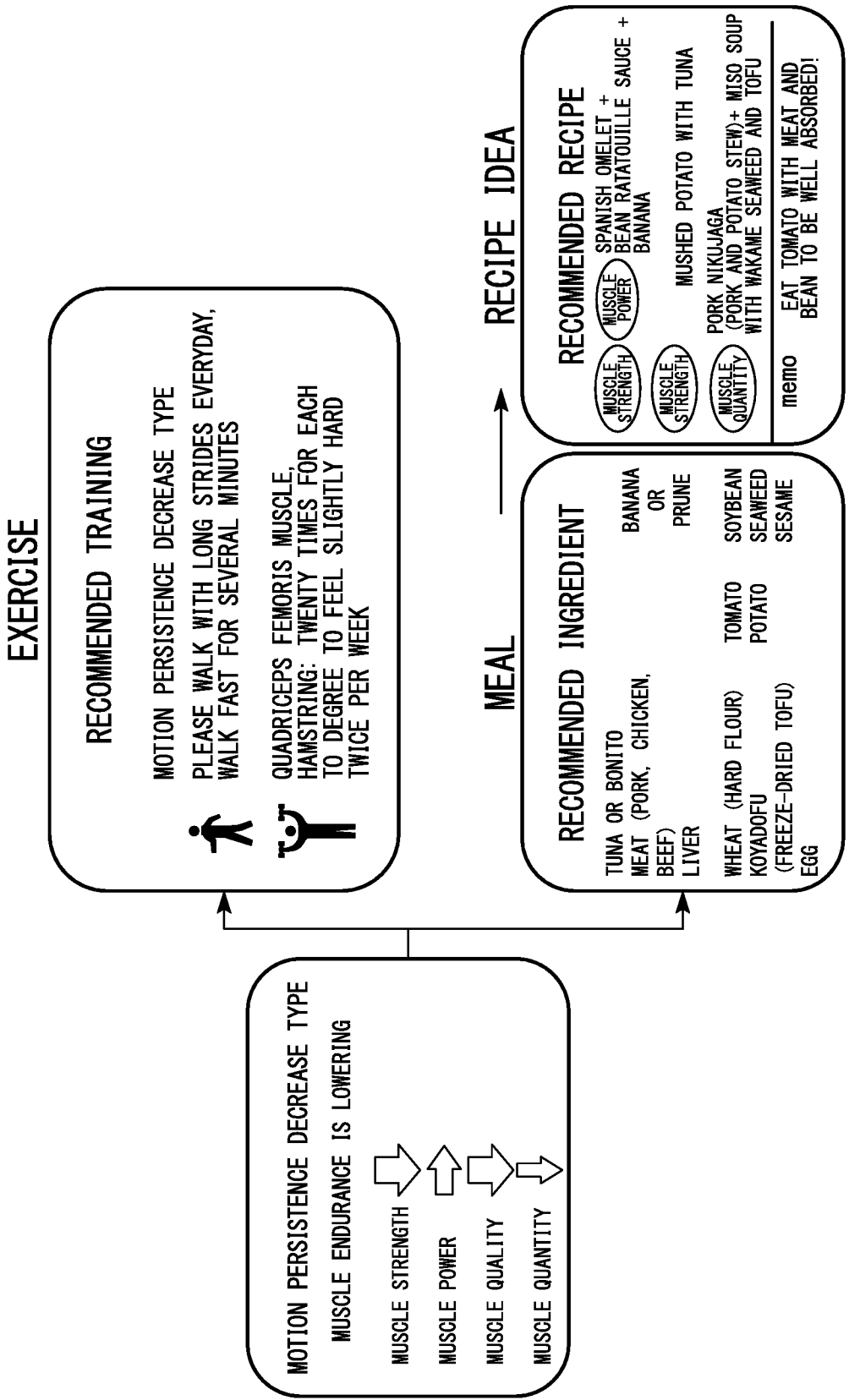
FIG. 19 is a view showing a second example of a display screen of the type of change in a muscle condition and a treatment, displayed by the display unit in the embodiment.

FIG. 19 is a view showing a second example of a display screen of the type of change in a muscle condition and a treatment, displayed by the display unit 210. FIG. 19 shows an example of a display screen in the case of the motion persistence decrease type (type D).

FIG. 19 shows changes of muscle strength, muscle power, muscle quality, and muscle quantity with arrows in addition to type name "motion persistence decrease type" as a display of type. Similarly to the case of FIG. 18, a downward wide arrow indicates a large decrease rate, and a downward narrow arrow indicates a small decrease rate. On the other hand, a lateral arrow indicates that muscle quantity is not reduced. That is, the lateral arrow indicates that muscle quantity is maintained.

Further, similarly to the case of FIG. 18, FIG. 19 shows training effective for the motion persistence decrease type as an exercise suggestion. FIG. 19 shows ingredients and recipes effective for the motion persistence decrease type for breakfast, lunch, and dinner as a nutrition suggestion.

The treatment determination unit 296 may also determine the timing when an exercise or nutrition ingestion is performed. For example, it is effective to ingest glycogen in the morning or after exercising. Therefore, the treatment determination unit 296 determines that glycogen is ingested at breakfast or after exercising. Then, the display unit 210 displays an exercise suggestion and a recipe corresponding to the condition that glycogen is ingested at breakfast or after walking.

As described above, the change information acquisition unit 293 acquires change information indicating changes in a plurality of muscle indicators. The type determination unit 295 determines the type of change in a muscle condition according to the change information.

In this way, the type determination unit 295 determines a type according to the change in a muscle condition, and thereby it is possible to perform a type determination in response to an occurring problem and to perform a type determination in response to a cause such as aging or no exercise. Thereby, it is possible to present a treatment effective for the muscle condition.

Further, the treatment determination unit 296 determines a treatment for the change in the muscle condition according to the type of change in the muscle condition determined by the type determination unit 295. Thereby, the treatment determination unit 296 can determine an effective treatment in response to the muscle condition.

Specifically, the treatment determination unit 296 can determine an effective exercise or meal in response to the muscle condition.

Further, the change information acquisition unit 293 acquires, as the change information, information indicating a change in muscle strength, a change in muscle power, a change in muscle quality, and a change in muscle quantity.

The type determination unit 295 determines a type of change in the muscle condition according to the change information, and thereby it is possible to perform a type classification in response to a cause such as aging or no exercise. The treatment determination unit 296 determines a treatment in response to the type classification and thereby can determine an effective treatment.

Further, the type determination unit 295 determines the type of change in the muscle condition by using a determination basis selected in response to the age of the user as a determination subject.

Thereby, the type determination unit 295 can reflect the effect of age on the muscle condition to the type determination.

In the above embodiment, a process performed by the motor function determination system 1 is described using an example in which a muscle function decreases such as muscle atrophy; however, the motor function determination system 1 may be applied to a case in which a muscle function improves such as muscle development. Specifically, the type determination unit 295 may determine the type of change in the muscle condition in a case where a muscle function decreases in addition to or in place of a case where a muscle function improves. Further, the treatment determination unit 296 may determine a treatment for the change in the muscle condition in a case where a muscle function decreases in addition to or in place of a case where a muscle function improves.

A program for realizing the function of the control unit 290 in part or in whole may be recorded in a computer-readable recording medium, and the program recorded in the recording medium may be read into and executed on a computer system to thereby perform the process of each unit. The "computer system" used herein includes an OS or hardware, such as peripheral devices.

The "computer system" also includes a homepage providing environment (or a display environment) when a WWW system is used.

The "computer-readable recording medium" refers to a portable medium such as a flexible disk, a magneto-optical disk, a ROM, or a CD-ROM, or a storage device such as a hard disk embedded in the computer system. Further, the "computer-readable recording medium" also includes a medium which dynamically holds a program for a short period of time, such as a communication line when the program is transmitted through a network, such as the Internet, or a communication line, such as a telephone line, and a medium which holds a program for a given period of time, such as a volatile memory in a computer system as a server or a client in the above case. Furthermore, the program described above may be a program which implements part of the functions described above, or may be a program which can implement the functions described above in combination with a program already recorded in the computer system.

Although the embodiment of the invention has been described in detail with reference to the drawings, specific configurations are not limited to the above-described embodiment and include design modification or the like without departing from the scope of the invention.

The invention claimed is:

1. A muscle condition change determination apparatus comprising:
   a memory;
   an interface circuit configured to acquire a bioelectrical impedance of a user that is measured by a bioelectrical impedance measurement circuit and a load which is associated with a motion of the user and which is measured by a load sensor; and
   a processor coupled to the memory and configured to:
      calculate a load applied on a measurement base, based on the load which is associated with the motion of the user and which is acquired by the interface circuit;
      calculate a plurality of different muscle indicators including:
         first and second muscle indicators based on the calculated load applied on the measurement base; and
         third and fourth muscle indicators based on the bioelectrical impedance of the user that is acquired by the interface circuit;

calculate a plurality of different change rates of the plurality of different muscle indicators based on each past value and each current value with respect to each of the plurality of different muscle indicators;

compare each of the plurality of calculated different change rates with a predetermined value;

acquire a plurality of comparison results each indicating a relationship between each of the plurality of calculated different change rates and the predetermined value; and classify a change in a muscle condition of the user into any of a plurality of types of change in a muscle condition that are stored in the memory based on a combination of the plurality of comparison results.

2. The muscle condition change determination apparatus according to claim 1,
wherein the processor is further configured to determine a treatment based on the classified change in the muscle condition.

3. The muscle condition change determination apparatus according to claim 1,
wherein the memory stores in advance an exercise effective for each type of change in a muscle condition that is classifiable by the processor in an associated manner, and
the processor suggests exercise behavior for the type of change in a muscle condition of the user that is classified by the processor based on the effective exercise which is stored in the memory and which is associated with each type of change in a muscle condition that is classifiable by the processor.

4. The muscle condition change determination apparatus according to claim 1,
wherein the memory stores in advance an ingredient and a recipe effective for each type of change in a muscle condition that is classifiable by the processor in an associated manner, and
the processor suggests nutrition behavior for the type of change in a muscle condition of the user that is classified by the processor based on the effective ingredient and the effective recipe which are stored in the memory and which are associated with each type of change in a muscle condition that is classifiable by the processor.

5. The muscle condition change determination apparatus according to claim 1,
wherein the motion of the user is a successive motion of sitting on a chair in a state where a foot is put on the measurement base, standing up from the state of sitting on the chair, and stabilizing a stagger of a body, and
the processor:
calculates, based on a load which is associated with the successive motion, a maximum value of the load applied on the measurement base, a maximum value of a change rate of a load, and a body weight; and
calculates a muscle strength indicator based on the maximum value of the load and the body weight, a muscle power indicator based on the maximum value of the change rate of the load and the body weight, a muscle quality indicator based on the bioelectrical impedance, and a muscle quantity indicator based on the bioelectrical impedance as the plurality of different muscle indicators.

6. The muscle condition change determination apparatus according to claim 1,
wherein the processor:
determines whether or not an age of the user is smaller than an age reference;

evaluates the muscle condition of the user based on a first determination reference in response to a determination that the age of the user is smaller than the age reference; and evaluates the muscle condition of the user based on a second determination reference that is different from the first determination reference in response to a determination that the age of the user is the age reference or more.

7. The muscle condition change determination apparatus according to claim 6,
wherein the first determination reference indicates:
determining whether or not a coefficient of fluctuation per day of the first muscle indicator and a coefficient of fluctuation per day of the second muscle indicator are smaller than a reference value,
the second determination reference that is different from the first determination reference indicates:
determining whether or not the coefficient of fluctuation per day of the first muscle indicator and the coefficient of fluctuation per day of the second muscle indicator are smaller than a first reference value; and
determining whether or not the coefficient of fluctuation per day of the first muscle indicator and the coefficient of fluctuation per day of the second muscle indicator are smaller than a second reference value that is different from the first reference value.

8. The muscle condition change determination apparatus according to claim 7,
wherein the processor evaluates that the change in a muscle condition of the user is a change in a muscle condition that corresponds to the age in response to a determination that:
the age of the user is the age reference or more; and
at least one of the coefficient of fluctuation per day of the first muscle indicator and the coefficient of fluctuation per day of the second muscle indicator is the first reference value or more.

9. The muscle condition change determination apparatus according to claim 7,
wherein the first muscle indicator is a muscle strength, and
the second muscle indicator is a muscle power.

10. The muscle condition change determination apparatus according to claim 9, comprising:
a display that displays the classified type of change in the muscle condition of the user.

11. The muscle condition change determination apparatus according to claim 9, comprising:
a display that displays a treatment for the change in the muscle condition of the user based on the classified type of change in the muscle condition of the user.

12. The muscle condition change determination apparatus according to claim 9,
wherein the first muscle indicator is a muscle strength indicator,
the second muscle indicator is a muscle power indicator,
the third muscle indicator is a muscle quality indicator, and
the fourth muscle indicator is a muscle quantity indicator.

13. The muscle condition change determination apparatus according to claim 1,
wherein the change in the muscle condition of the user is classified into any of the plurality of types of change in the muscle condition that are stored in the memory based on a combination of the plurality of comparison results including at least:

a first comparison result that indicates a relationship between the calculated change rate of the first muscle indicator and a first value as the predetermined value;

a second comparison result that indicates a relationship between the calculated change rate of the second muscle indicator and a second value as the predetermined value; and a third comparison result that indicates a relationship between the calculated change rate of the third muscle indicator and a third value as the predetermined value.

14. The muscle condition change determination apparatus according to claim 13, wherein the first muscle indicator is a muscle strength indicator, the second muscle indicator is a muscle power indicator, the third muscle indicator is a muscle quality indicator, and the fourth muscle indicator is a muscle quantity indicator.

15. The muscle condition change determination apparatus according to claim 1, wherein the change in the muscle condition of the user is classified into any of the plurality of types of change in the muscle condition that are stored in the memory based on a combination of the plurality of comparison results which are a first comparison result that indicates a relationship between the calculated change rate of the first muscle indicator and a first value as the predetermined value, a second comparison result that indicates a relationship between the calculated change rate of the second muscle indicator and a second value as the predetermined value, a third comparison result that indicates a relationship between the calculated change rate of the third muscle indicator and a third value as the predetermined value, and a fourth comparison result that indicates a relationship between the calculated change rate of the fourth muscle indicator and a fourth value as the predetermined value.

16. The muscle condition change determination apparatus according to claim 15, wherein the first muscle indicator is a muscle strength indicator, the second muscle indicator is a muscle power indicator, the third muscle indicator is a muscle quality indicator, and the fourth muscle indicator is a muscle quantity indicator.

17. A muscle condition change determination method comprising:

acquiring a bioelectrical impedance of a user that is measured by a bioelectrical impedance measurement circuit and a load which is associated with a motion of the user and which is measured by a load sensor via an interface circuit;

calculating a load applied on a measurement base, based on the acquired load which is associated with the motion of the user and which is acquired by the interface circuit;

calculating a plurality of different muscle indicators including:

first and second muscle indicators based on the calculated load applied on the measurement base; and third and fourth muscle indicators based on the bioelectrical impedance of the user that is acquired by the interface circuit;

calculating a plurality of different change rates of the plurality of different muscle indicators based on each past value and each current value with respect to each of the plurality of different muscle indicators;

comparing each of the plurality of calculated different change rates with a predetermined value;

acquiring a plurality of comparison results each indicating a relationship between each of the plurality of calculated different change rates and the predetermined value; and classifying a change in a muscle condition of the user into any of a plurality of types of change in a muscle condition that are stored in the memory based on a combination of the plurality of comparison result.

18. A non-transitory computer-readable recording medium comprising a program that causes a computer to:

acquire a bioelectrical impedance of a user that is measured by a bioelectrical impedance measurement circuit and a load which is associated with a motion of the user and which is measured by a load sensor via an interface circuit;

calculate a load applied on a measurement base, based on the acquired load which is associated with the motion of the user and which is acquired by the interface circuit;

calculating a plurality of different muscle indicators including:

first and second muscle indicators based on the calculated load applied on the measurement base; and third and fourth muscle indicators based on the bioelectrical impedance of the user that is acquired by the interface circuit;

calculating a plurality of different change rates of the plurality of different muscle indicators based on each past value and each current value with respect to each of the plurality of different muscle indicators;

comparing each of the plurality of calculated different change rates with a predetermined value;

acquiring a plurality of comparison results each indicating a relationship between each of the plurality of calculated different change rates and the predetermined value; and classifying a change in a muscle condition of the user into any of a plurality of types of change in a muscle condition that are stored in the memory based on a combination of the plurality of comparison result.

* * * * *